United States Patent … US 8,111,905 B2
Campbell … Date of Patent: Feb. 7, 2012

(54) AUTOFOCUS VIDEO TOOL AND METHOD FOR PRECISE DIMENSIONAL INSPECTION

(75) Inventor: Shannon R. Campbell, Bothell, WA (US)

(73) Assignee: Mitutoyo Corporation, Kawasaki-shi (JP)

( * ) Notice: Subject to any disclaimer, the term of this patent is extended or adjusted under 35 U.S.C. 154(b) by 278 days.

(21) Appl. No.: 12/608,943

(22) Filed: Oct. 29, 2009

(65) Prior Publication Data

US 2011/0103679 A1    May 5, 2011

(51) Int. Cl.
*G06K 9/00* (2006.01)

(52) U.S. Cl. ........ 382/152; 382/100; 382/255; 382/325; 348/86; 348/E7.085

(58) Field of Classification Search .................. 382/100, 382/152, 255, 325; 348/86, E7.085
See application file for complete search history.

(56) References Cited

U.S. PATENT DOCUMENTS

| | | | |
|---|---|---|---|
| 5,200,828 A | 4/1993 | Jang | |
| 5,398,096 A | 3/1995 | Yagoto | |
| 5,790,710 A | 8/1998 | Price | |
| 5,892,218 A | 4/1999 | Ortyn | |
| 6,239,554 B1 | 5/2001 | Tessadro | |
| 6,542,180 B1 | 4/2003 | Wasserman | |
| 6,608,705 B1 | 8/2003 | Oshima | |
| 6,627,863 B2 | 9/2003 | Wasserman | |
| 6,975,810 B2 | 12/2005 | Iwane | |
| 7,030,351 B2 | 4/2006 | Wasserman | |
| 7,324,682 B2 | 1/2008 | Wasserman | |
| 7,454,053 B2 * | 11/2008 | Bryll et al. ................... 382/152 |
| 7,570,795 B2 * | 8/2009 | Yu et al. ........................ 382/141 |
| 7,724,942 B2 * | 5/2010 | Bryll ............................. 382/151 |
| 2003/0197925 A1 | 10/2003 | Hamborg | |
| 2005/0031191 A1 | 2/2005 | Venkatachalam | |
| 2005/0213807 A1 * | 9/2005 | Wasserman ................... 382/152 |
| 2006/0001955 A1 | 1/2006 | Kinney | |

(Continued)

FOREIGN PATENT DOCUMENTS

EP    1 381 229 A1    1/2004

(Continued)

OTHER PUBLICATIONS

Bryll, R.K., and M. Nahum, "System and Method for Fast Approximate Focus," U.S. Appl. No. 12/343,383, filed Dec. 23, 2008.

(Continued)

*Primary Examiner* — Stephen Koziol
(74) *Attorney, Agent, or Firm* — Christensen O'Connor Johnson Kindness PLLC

(57) ABSTRACT

A refined autofocus method provides optimized lighting between iterative autofocus operations, to reliably provide the best possible autofocus Z-height precision. The method includes a quantitative initial focus Z-height determination based on initial focus curve data from initial autofocus images acquired using initial light control parameters. Then, the camera is set at that initial focus Z-height such that well focused images are provided. Refined (optimized) light control parameters are then determined based on at least one respective image acquired using respective light control parameters at that Z-height, such that an image acquired using the refined light control parameters provides a near-optimum value for a contrast-related metric (e.g., a focus metric) at that Z-height. Then, refined autofocus images are acquired using the refined light control parameters and a refined precise Z-height is quantitatively determined base on the resulting focus curve.

11 Claims, 10 Drawing Sheets

U.S. PATENT DOCUMENTS

| | | |
|---|---|---|
| 2006/0012836 A1 | 1/2006 | Boemler |
| 2006/0093205 A1* | 5/2006 | Bryll et al. .................. 382/152 |
| 2008/0019683 A1 | 1/2008 | Yu |
| 2009/0086046 A1 | 4/2009 | Reilly |

FOREIGN PATENT DOCUMENTS

| | | |
|---|---|---|
| WO | 00/75709 A1 | 12/2000 |

OTHER PUBLICATIONS

Geusebroek, J.-M., et al., "Robust Autofocusing in Microscopy," ISIS Technical Report Series, vol. 17, Intelligent Sensory Information Systems Group, University of Amsterdam, Nov. 2000, 20 pages.

Krotkov, E., "Focusing," International Journal of Computer Vision, 1:223-237, 1987.

"QVPAK 3D CNC Vision Measuring Machine: Operating Guide," Version 2.0, Manual No. 4911GB, Series No. 359, Mitutoyo Corporation & Micro Encoder Inc., Kanagawa, Japan, Sep. 1996.

"QVPAK 3D CNC Vision Measuring Machine: User's Guide," Version 7.1, 2nd ed., Manual No. 99MCB225A1, Series No. 359, Mitutoyo Corporation & Micro Encoder Inc., Kanagawa, Japan, Sep. 2003.

West, P.C., "High Speed, Real-Time Machine Vision," CyberOptics—Imagenation, Portland, Ore., 2001, 39 pages.

* cited by examiner

AUTOFOCUS VIDEO TOOL AND METHOD FOR PRECISE DIMENSIONAL INSPECTION

FIELD OF THE INVENTION

The invention relates generally to machine vision inspection systems, and more particularly to video tools and methods for precise dimensional inspection.

BACKGROUND OF THE INVENTION

Precision machine vision inspection systems (or "vision systems" for short) can be utilized to obtain precise dimensional measurements of inspected objects and to inspect various other object characteristics. Such systems may include a computer, a camera and optical system, and a precision stage that is movable in multiple directions to allow workpiece inspection. One exemplary prior art system, that can be characterized as a general-purpose "off-line" precision vision system, is the commercially available QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the *QVPAK 3D CNC Vision Measuring Machine User's Guide*, published January 2003, and the *QVPAK 3D CNC Vision Measuring Machine Operation Guide*, published September 1996, each of which is hereby incorporated by reference in their entirety. This type of system is able to use a microscope-type optical system and move the stage so as to provide inspection images of either small or relatively large workpieces at various magnifications.

General purpose precision machine vision inspection systems, such as the QUICK VISION™ system, are also generally programmable to provide automated video inspection. Such systems typically include GUI features and predefined image analysis "video tools" such that operation and programming can be performed by "non-expert" operators. For example, U.S. Pat. No. 6,542,180, issued Apr. 1, 2003 (hereinafter "the '180 patent") which is incorporated herein by reference in its entirety, teaches such a vision system that uses automated video inspection. Video tools may be called simply "tools", for short. For example, edge detection tools may include point tools for detecting a point on an edge, box tools for detecting the location and direction of an edge located in a region of interest defined by the box tool, and so on.

As taught in the '180 patent, automated video inspection metrology instruments generally have a programming capability that allows an automatic inspection event sequence to be defined by the user for each particular workpiece configuration. Such programming can be implemented as text-based programming, or through a recording mode that progressively "learns" the inspection event sequence by storing a sequence of machine control instructions and individual video tool parameters corresponding to a sequence of inspection operations defined and/or performed by a user (e.g., with the aid of various semi-automatic or automatic video tool operations), or through a combination of both methods. Such a recording mode is often referred to as "learn mode" or "training mode". In either technique, the machine control instructions and individual video tool parameters are generally stored as a part program that is specific to the particular workpiece configuration, and automatically performs a predetermined sequence of inspection operations during a "run mode" of operation.

Z-height measurements (along the optical axis and focusing axis of the camera system) are generally derived from a "best focus" position, such as that determined by an autofocus tool or method. In general, according to prior art autofocus methods and/or tools, the camera moves through a range of positions along a Z-axis (the focusing axis) and captures an image at each position. For each captured image, a focus metric is calculated based on the image and related to the corresponding position of the camera along the Z-axis at the time that the image was captured. This results in a focus curve data, which may be referred to simply as a "focus curve" or "autofocus curve". The peak of the focus curve, which corresponds to the best focus position along the Z-axis, may be found by fitting a curve to the focus curve data and estimating the peak of the fitted curve. One known method of autofocusing similar to that outlined above is discussed in "Robust Autofocusing in Microscopy", by Jan-Mark Geusebroek and Arnold Smeulders in ISIS Technical Report Series, Vol. 17, November 2000, which is hereby incorporated herein by reference in its entirety. The disclosed method teaches that the video hardware captures frames at a fixed rate, and that the sampling density of the focusing curve can be influenced by adjusting the stage velocity. Another known autofocus method and apparatus is described in U.S. Pat. No. 5,790,710, issued Aug. 4, 1998 (hereinafter "the '710 patent") which is hereby incorporated by reference in its entirety. In the '710 patent a piezoelectric positioner is utilized in conjunction with a conventional motor-driven motion control system to control the Z-axis position motion while acquiring autofocus images. Another improved autofocus system and method is described in U.S. Pat. No. 7,030,351, issued Apr. 18, 2006 (hereinafter "the '351 patent") which is commonly assigned and hereby incorporated by reference in its entirety.

Measurement accuracy and repeatability in the micron or submicron range are routinely obtained along the X and Y axes, in the plane of the inspection images used by precision machine vision inspection systems. However, the level of accuracy and repeatability achieved for Z-height measurements, based on autofocus tools or operations, is generally less than that achieved for other measurement axes in precision machine vision inspection systems. It would be desirable for an autofocus tool to operate automatically with improved accuracy, repeatability and robustness, in order to allow more accurate and/or repeatable Z-height measurements to be determined.

SUMMARY OF THE INVENTION

This summary is provided to introduce a selection of concepts in a simplified form that are further described below in the Detailed Description. This summary is not intended to define key features of the claimed subject matter, nor is it intended to be used as an aid in determining the scope of the claimed subject matter.

The critical nature of the interaction of image focus and lighting optimization has not been fully recognized or addressed in machine vision inspection systems, particularly in relation to the highest achievable levels of autofocus video tool accuracy and/or repeatability and robustness, and particularly in relation to certain surface finishes and/or patterns. Typical prior art autofocus methods have determined image acquisition light settings by qualitative user light setting or, if the user chooses, by lighting adjustment tools which operate independently of an autofocus tool. For example, lighting adjustment tools which operate independently of an autofocus tool are disclosed in the previously incorporated '180 patent, and in U.S. Pat. No. 6,627,863, issued Sep. 30, 2003

(hereinafter "the '863 patent") which is commonly assigned and hereby incorporated herein by reference in its entirety. Briefly, the '180 patent teaches a multi area image quality tool that allows the user to specify the location, orientation and size of two or more regions of interest around a critical feature (e.g., an edge between the two regions), and to specify the light sources to be used to illuminate the part, the image quality to be measured (e.g., contrast across an edge), and a range of acceptable values for that image quality. The multi-area image quality tool may then automatically adjust the light source brightness to achieve an acceptable value for the image quality. The '863 patent teaches simulating an image based on a number of base images and a current lighting vector. An actual workpiece is imaged using one of the various illumination sources of a vision system. Then at least two base images of the object are captured, where each base image is illuminated using a different illumination intensity. This is repeated for each different illumination source provided in the vision system. Simulated images are then generated by combining various ones of the base images based on the light intensities of the light sources prescribed in a current lighting vector. Each simulated image can be evaluated to determine if it has a desired image quality (e.g., a desired brightness level and/or contrast). The current lighting vector can be automatically modified until a simulated image having the desired image quality is obtained. That lighting vector can then be used to obtain a well lighted actual image.

However, since the critical nature of the interaction of image focus and lighting optimization has not been fully recognized or addressed, the light setting tools outlined above have not been properly integrated into an autofocus tool, or configured to operate in conjunction with an autofocus tool in a way that reliably provides the highest achievable levels of autofocus repeatability and accuracy. For example, with regard to autofocus repeatability, FIG. 3 shows a graph 300 illustrating representative autofocus repeatability in relation to light level, for a workpiece surface in a precision machine vision inspection system. As shown in FIG. 3, there is a relatively broad range of lighting 310 where a good level of repeatability may be obtained in the corresponding repeatability range 320 (e.g., better than 0.3 microns). Typical prior art autofocus methods have provided lighting within the broad range 310 by qualitative user light setting or lighting adjustment tools which operate independently of an autofocus tool, but autofocus tools have not reliably enforced lighting within an optimized range 330 that corresponds to the best level of repeatability 340 (e.g., on the order of 0.2 microns). Various related considerations are discussed in greater detail below with reference to FIG. 3. In addition to repeatability considerations, non-optimized autofocus lighting may degrade Z-height measurement accuracy, particularly when the lighting results in saturated pixels. Furthermore, optimized autofocus lighting cannot be reliably established except in a well focused image, so an iterative method of focusing and light setting is required in order to optimize autofocus results. Such considerations are discussed in greater detail below, particularly with reference to FIG. 5.

The present invention provides a method for optimized autofocus lighting (e.g., within the optimized lighting range 330) that may be used in conjunction with an autofocus video tool that reliably provides autofocus accuracy and/or repeatability and/or robustness at a level not reliably obtained in the prior art (e.g., within the optimized repeatability range 340). As described in greater detail below, this method for reliable and robust determination of fully optimized autofocus lighting enforces providing and analyzing very well focused images (e.g., images focused using a quantitative focus analysis).

As previously outlined, autofocus methods are often based on determining and analyzing a focus curve to find its peak. Determining a focus curve generally comprises plotting the value of an image focus metric (e.g., a contrast metric) as a function of the focus distance from the camera to the workpiece, based on a series of images taken at different focusing distances. In the prior art, autofocus operations (e.g., as embodied in autofocus video tools) have typically utilized the same lighting throughout an entire set of autofocus operations leading to an autofocus position.

In contrast, in various embodiments disclosed herein, a set of autofocus operations includes an initial quantitative autofocus performed using an initial lighting configuration and/or light level for the associated set of initial autofocus images, which are used as the basis for an initial focus curve. In some embodiments, the initial lighting configuration is determined such that it is not optimized, but it is certain that saturated image pixels are avoided in the initial autofocus images. Then, the camera is set at an initial focus distance corresponding approximately to the peak of the initial focus curve, and a refined lighting configuration (e.g., a refined set of light control parameters and/or light level) are determined and/or learned such that the resulting image provides an improved level (e.g., a desired or near-optimum level) of the image focus metric that is used in the focus curve, or an image characteristic that is correlated with that image focus metric, at that initial focus distance. Then, a second or final autofocus is performed using the refined lighting configuration for an associated set of final autofocus images. In some embodiments, specific precautions are taken to avoid saturated pixels when setting the refined lighting configuration, as described in greater detail below. Because the value of the image focus metric will be higher in the set of final autofocus images, the focus curve will have a higher peak value and a better signal to noise ratio, so that the focus curve peak and the resulting autofocus position may be determined with a higher level of accuracy and/or repeatability.

In accordance with one aspect of the invention, an autofocus method is provided that uses iterative autofocus peak finding operations, wherein a lighting refinement is performed after an initial quantitative focus peak finding process, and before a final quantitative focus peak finding process.

In accordance with a further aspect of the invention, in some embodiments, the refined lighting configuration is determined such that it is certain that relatively few or no image pixels are saturated in an image at the initial focus distance.

In one embodiment, the final autofocus curve is determined using relatively fine steps between the associated set of autofocus images along the Z-axis, further enhancing the estimate of its peak location. In one embodiment, an initial focus curve is determined based on relatively "sparsely sampled" or widely separated (along the Z-axis) images which can be acquired and analyzed to determine a focus peak location relatively quickly.

In one embodiment, the set of refined light control parameters are determined corresponding to an autofocus region of interest (e.g., a region of interest defined using an autofocus tool) during a learn mode of operation of the machine vision inspection system, and the system then stores the set of refined light control parameters (e.g., in a part program) for later use when determining focus curve data for a corresponding autofocus region of interest (at a corresponding location on a corresponding workpiece) during a run mode. In one implementation, referred to herein as a learn-mode governed implementation, the stored set of refined light control parameters are used unchanged for determining a single and final set of focus curve data and associated Z-height and/or focus location for a corresponding autofocus region of interest (at a corresponding location on a corresponding workpiece) during a run mode. In one implementation, referred to herein as a run-mode refinement implementation, the stored set of refined light control parameters determined during learn mode are used as an initial light setting for determining an initial set of focus curve data for a corresponding autofocus region of interest during run mode operation. Then, the camera is set at an initial run mode focus distance corresponding approximately to the peak of the initial focus curve, and a refined lighting configuration is determined (e.g., the lighting configuration and/or individual light levels are adjusted) such that the resulting image provides an improved level for the image focus metric at that initial focus distance. Then, a second or final autofocus is performed during run mode, using the refined lighting configuration for an associated set of final autofocus images and resulting focus curve, which results in the best possible run mode autofocus accuracy and/or repeatability. In a variation of this implementation, referred to herein as a conditional run-mode refinement implementation, after the initial set of focus curve data are determined, the value of an associated image focus metric (e.g., the peak focus metric), or an image metric correlated with that image focus metric, is determined. If the value of that associated image metric is sufficient to indicate that initial set of focus curve data corresponds to sufficiently optimal lighting (e.g., if the run mode image metric is close to the value of a comparable metric determined and stored during learn mode), then the tool operates similarly to the learn-mode governed implementation, and that initial set of focus curve data is used as a single and final set of focus curve data for determining the Z-height and/or focus location associated with that autofocus tool. However, if the value of that associate image metric is not sufficient to indicate that initial set of focus curve data corresponds to sufficiently optimal lighting, then the tool operates similarly to the run-mode refinement implementation. That is, the camera is set at an initial run mode focus distance corresponding approximately to the peak of the initial focus curve, and a refined lighting configuration is determined (e.g., the lighting configuration and/or individual light levels are adjusted) such that the resulting image provides an improved level for the image focus metric at that initial focus distance. Then, a second or final autofocus is performed during run mode, using the refined lighting configuration for an associated set of final autofocus images and resulting focus curve. It will be appreciated that this implementation ensures fast part program execution if there is little variation between workpieces and their images, and also conditionally provides optimal run mode lighting adjustments for robust high accuracy autofocus and/or Z-height determination in case there are significant run mode variations between workpiece images as a result of workpiece variations or lighting system variations, or the like.

In another embodiment, a set of refined light control parameters are not determined during learn mode. Rather, in an implementation referred to herein as a run-mode originated implementation, a set of learn mode lighting parameters are determined and stored for a particular autofocus tool and region of interest (e.g., in a part program) according to a previously known method. However, the autofocus tool or autofocus tool mode set during learn mode implements the previously outlined iterative focus and lighting steps for that tool during run mode. That is, during run mode, for that tool the initial stored lighting configuration (e.g., as defined in the part program) is used for an associated set of initial autofocus images that are the basis for an initial focus curve determined during run mode. Then, the camera is set at an initial focus distance corresponding approximately to the peak of that initial run mode focus curve, and a refined lighting configuration is determined such that the resulting image provides an improved level of the image focus metric that is used in the focus curve (or an image characteristic that is correlated with that image focus metric) at that initial focus distance. Then, a second or final autofocus and/or Z-height determination is performed for that autofocus tool using the refined lighting configuration for an associated set of final autofocus images.

In accordance with another aspect of the invention, autofocus tool mode determining operations may be provided that determine which of the aforementioned precision autofocus tool implementations, if any, are associated with an autofocus tool (e.g., during manual mode, or learn mode, or as recorded in a part program). In some embodiments, the autofocus tool mode determining operations include the user determining the autofocus tool mode. In some embodiments, the autofocus tool mode determining operations include learn mode operations that determine and analyze a lighting sensitivity curve, as described in greater detail with reference to FIG. 5.

It will be appreciated that, while the increase in accuracy of the autofocus operations is particularly useful with regard to determining highly accurate Z-height values, that the improved autofocus accuracy may also help increase the accuracy of other measurement operations (e.g., the operation of edge locating tools, etc.). The increase in accuracy and repeatability of Z-height values and/or autofocus may be relatively significant for certain surface textures and/or texture variations. In addition, while the increase in accuracy and repeatability may in some instances be relatively small (e.g., sub-micron for certain magnifications), it will be appreciated that even small improvements in the repeatability, accuracy and/or robustness of such autofocus operations are difficult to obtain in numerous applications, yet highly valued. In addition, in all cases greater accuracy is generally more desirable when performing precision measurement operations.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
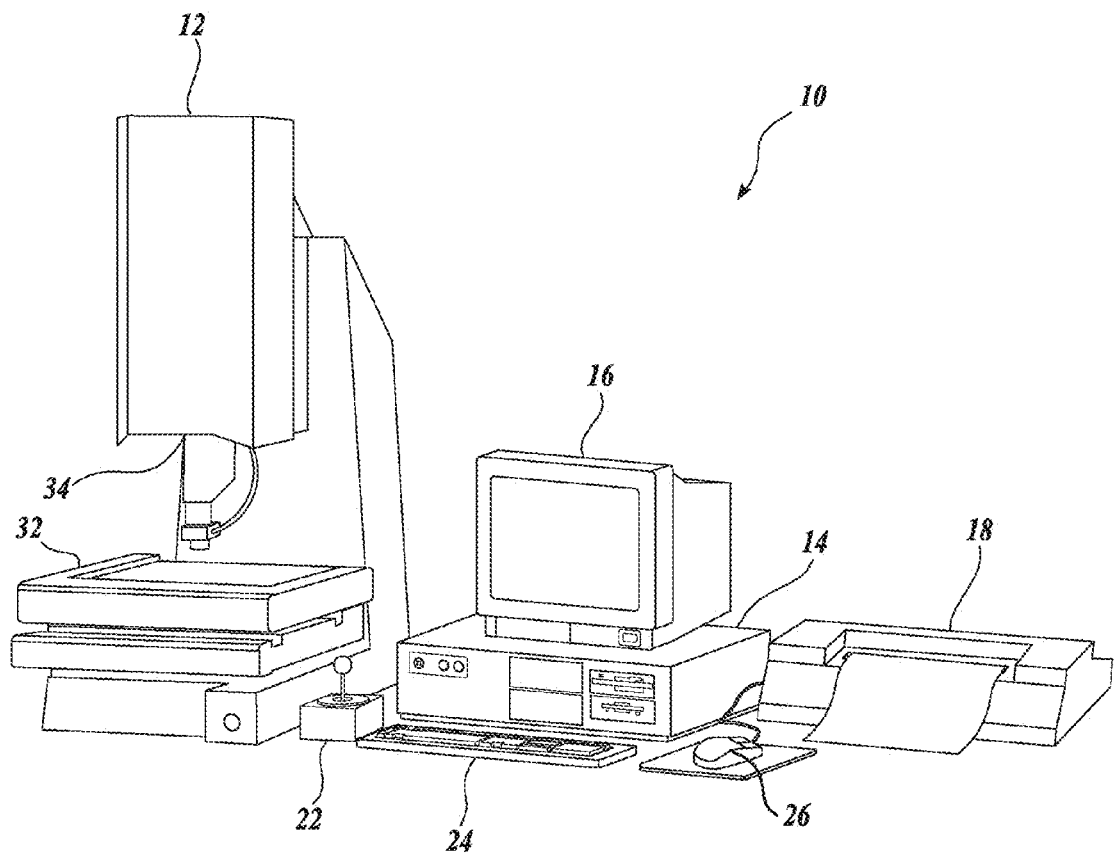
FIG. 1 is a diagram showing various typical components of a general purpose precision machine vision inspection system.

FIG. 1 is a block diagram of one exemplary machine vision inspection system 10 usable in accordance with the present invention. The machine vision inspection system 10 includes a vision measuring machine 12 that is operably connected to exchange data and control signals with a controlling computer system 14. The controlling computer system 14 is further operably connected to exchange data and control signals with a monitor or display 16, a printer 18, a joystick 22, a keyboard 24, and a mouse 26. The monitor or display 16 may display a user interface suitable for controlling and/or programming the operations of the machine vision inspection system 10.

The vision measuring machine 12 includes a moveable workpiece stage 32 and an optical imaging system 34 which may include a zoom lens or interchangeable lenses. The zoom lens or interchangeable lenses generally provide various magnifications for the images provided by the optical imaging system 34. The machine vision inspection system 10 is generally comparable to the QUICK VISION® series of vision systems and the QVPAK® software discussed above, and similar state-of-the-art commercially available precision machine vision inspection systems. The machine vision inspection system 10 is also described in commonly assigned U.S. Pat. No. 7,454,053, issued Nov. 18, 2008, and in co-pending and commonly assigned U.S. patent application Ser. No. 12/343,383, filed Dec. 23, 2008, and published under Pre-Grant Publication No. 2010/0158343 A1, which are each hereby incorporated herein by reference in their entireties. Various aspects of vision measuring machines and control systems are also described in more detail in co-pending and commonly assigned U.S. patent application Ser. No. 10/632,823, filed Aug. 4, 2003, and published under Pre-Grant Publication No. 2005/0031191 A1, and U.S. Pat. No. 7,324,682, issued Jan. 29, 2008, which are also each hereby incorporated herein by reference in their entireties. The refined lighting autofocus operations disclosed herein can increase measurement accuracy for certain applications of machine vision inspection systems. Furthermore, the methods may be implemented as an easy to use video tool and/or autofocus mode of operation.

Figure 2:
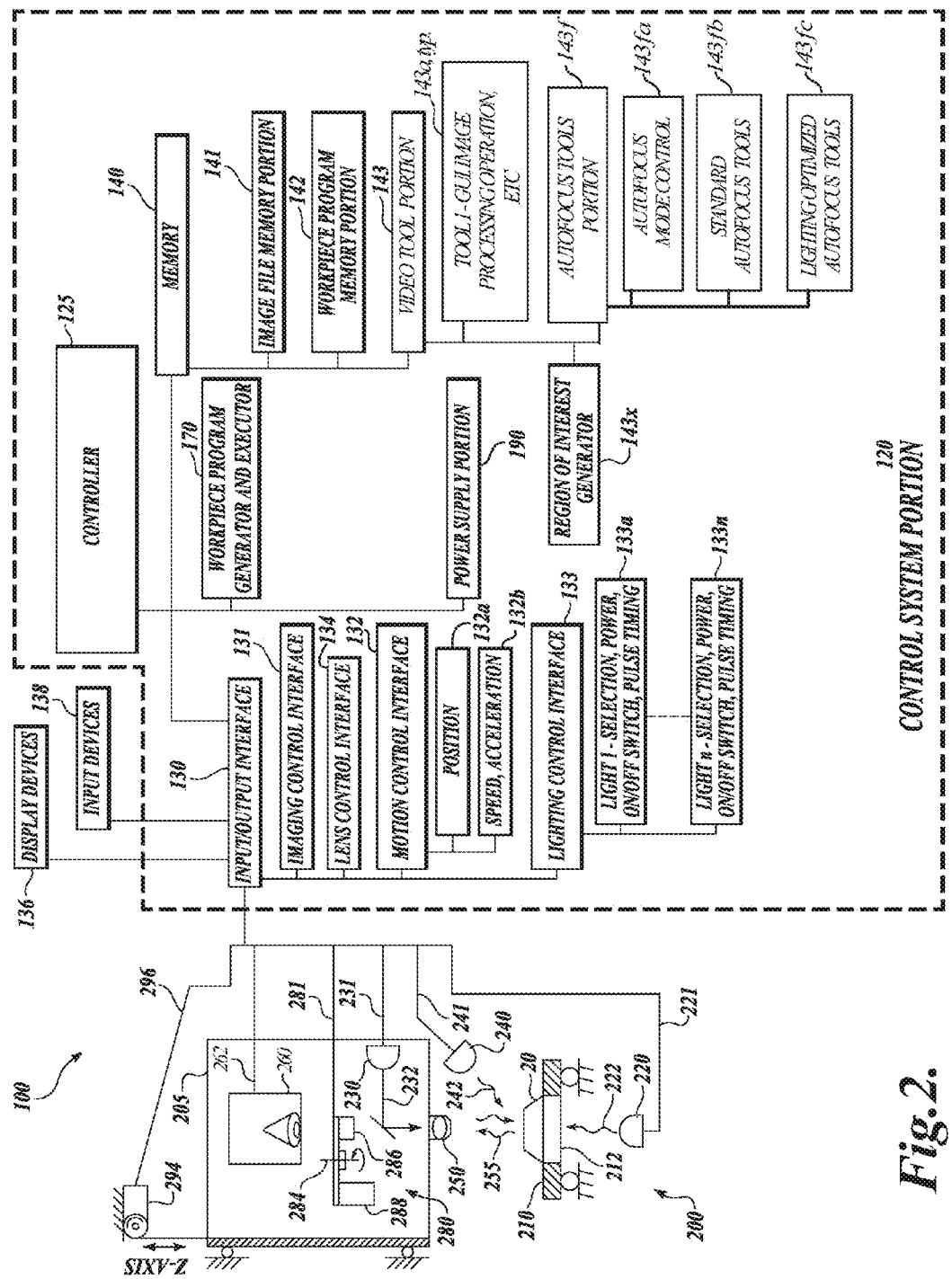
FIG. 2 is a block diagram of a control system portion and a vision components portion of a machine vision inspection system.

FIG. 2 is a block diagram of a control system portion 120 and a vision components portion 200 of a machine vision inspection system 100 in accordance with the present invention. As will be described in more detail below, the control system portion 120 is utilized to control the vision components portion 200. The vision components portion 200 includes an optical assembly portion 205, light sources 220, 230 and 240, and a workpiece stage 210 having a central transparent portion 212. The workpiece stage 210 is controllably movable along X and Y axes that lie in a plane that is generally parallel to the surface of the stage where a workpiece 20 may be positioned. The optical assembly portion 205 includes a camera system 260, an interchangeable objective lens 250, and may include a turret lens assembly 280 having lenses 286 and 288, and the co-axial light source 230. Alternatively to the turret lens assembly, a fixed or manually interchangeable magnification-altering lens, or a zoom lens configuration, or the like, may be included. The optical assembly portion 205 is controllably movable along a Z-axis that is generally orthogonal to the X and Y axes, by using a controllable motor 294, as described further below.

A workpiece 20 that is to be imaged using the machine vision inspection system 100 is placed on the workpiece stage 210. One or more of a stage light 220, a co-axial light 230, and a surface light 240 may emit source light 222, 232, or 242, respectively, to illuminate the workpiece 20. The source light is reflected or transmitted as workpiece light 255, which passes through the interchangeable objective lens 250 and the turret lens assembly 280 and is gathered by the camera system 260. The image of the workpiece 20, captured by the camera system 260, is output on a signal line 262 to the control system portion 120. The light sources 220, 230, and 240 may be connected to the control system portion 120 through signal lines or busses 221, 231, and 241, respectively. To alter the image magnification, the control system portion 120 may rotate the turret lens assembly 280 along axis 284, to select a turret lens, through a signal line or bus 281.

In various exemplary embodiments, the optical assembly portion 205 is movable in the vertical Z-axis direction relative to the workpiece stage 210 using a controllable motor 294 that drives an actuator, a connecting cable, or the like, to move the optical assembly portion 205 along the Z-axis to change the focus of the image of the workpiece 20 captured by the camera system 260. The term Z-axis, as used herein, refers to the axis that is intended to be used for focusing the image obtained by the optical assembly portion 205. The controllable motor 294, when used, is connected to the input/output interface 130 via a signal line 296.

As shown in FIG. 2, in various exemplary embodiments, the control system portion 120 includes a controller 125, an input/output interface 130, a memory 140, a workpiece program generator and executor 170, and a power supply portion 190. Each of these components, as well as the additional components described below, may be interconnected by one or more data/control buses and/or application programming interfaces, or by direct connections between the various elements.

The input/output interface 130 includes an imaging control interface 131, a motion control interface 132, a lighting control interface 133, and a lens control interface 134. The motion control interface 132 may include a position control element 132a, and a speed/acceleration control element 132b. However, it should be appreciated that in various exemplary embodiments, such elements may be merged and/or indistinguishable. The lighting control interface 133 includes lighting control elements 133a-133n, which control, for example, the selection, power, on/off switch, and strobe pulse timing if applicable, for the various corresponding light sources of the machine vision inspection system 100.

The memory 140 includes an image file memory portion 141, a workpiece program memory portion 142 that may include one or more part programs, or the like, and a video tool portion 143. The video tool portion 143 includes tool portion 143a, and other similar tool portions (not shown), which determine the GUI, image processing operation, etc., for each of the corresponding tools. The video tool portion 143 also includes a region of interest generator 143x that supports automatic, semi-automatic and/or manual operations that define various ROIs that are operable in various video tools included in the video tool portion 143.

In particular, in various embodiments according to this invention, the video tool portion 143 includes the autofocus tools portion 143f, which provides various operations and features related to autofocus operations, as described in greater detail below. In one embodiment, the autofocus tools portion 143f may include an autofocus mode control 143fa, standard autofocus tools 143fb, and lighting optimized autofocus tools 143fc. Briefly, the standard autofocus tools 143fb may operate similarly to known autofocus tools, for example, performing operations in learn mode and run mode such as utilizing a selected lighting level for acquiring a current image stack at various Z-heights, generating all or part of a focus curve, and finding its peak as a best focus position. The lighting optimized autofocus tools 143fc operate based on the refined lighting methods of the present invention. In contrast to the standard autofocus tools 143fb, in one example embodiment the lighting optimized autofocus tools 143fc perform an initial autofocus peak finding process utilizing an initial lighting configuration and/or level and then, after moving to focus at the initial autofocus peak location, a refined lighting configuration and/or level is determined (in other words, a set of refined light control parameters are determined). In one implementation, after the set of refined light control parameters are determined and the lighting is adjusted to a more optimum level, then a final autofocus peak finding process is performed using the refined lighting setting to achieve more accurate and/or robust Z-height determination and/or autofocus results. The autofocus mode control 143fa may perform operations, as disclosed herein, to configure the autofocus tools (that is the standard autofocus tools 143fb or the lighting optimized autofocus tools 143fc) or tool modes, depending on which tool or mode is activated. The descriptor "lighting optimized" of the autofocus tools 143fc is not intended to be limiting, it is intended to encompass any autofocus tools that enforce determination of improved or refined light settings that are determined as disclosed herein (e.g., refined light settings determined after initial autofocus peak finding operations), and is chosen primarily to emphasize a difference in lighting determination relative to the lighting of the standard autofocus tools 143fb, which do not perform the iterative autofocus peak finding step for determining refined lighting parameters.

Alternative configurations are possible for the autofocus tools portion 143f. For example, the standard autofocus tools 143fb and the lighting optimized autofocus tools 143fc may include partitioned mode control functions such that a separate mode control portion 143fa may be omitted. Alternatively, the autofocus tools portion 143f may provide one or more generic autofocus tool elements, and the mode control portion 143fa may provide operations that govern the user interface and interrelationships of the generic autofocus tool elements in a manner that depends on whether standard autofocus tool behavior, or lighting optimized autofocus tool behavior, is desired. In such a case, the circuits, routines, or applications that provide the operations of the standard autofocus tools 143fb, and/or the lighting optimized autofocus tools 143fc, may be merged and/or indistinguishable. In certain implementations, the autofocus mode control 143fa may be utilized to implement a lighting optimized autofocus mode (as opposed to a separate tool). More generally, this invention may be implemented in any now known or later-developed form that is operable in conjunction with the machine vision inspection system 100 to provide the features disclosed herein in relation to the refined lighting autofocus operations.

In general, the memory portion 140 stores data usable to operate the vision system components portion 200 to capture or acquire an image of the workpiece 20 such that the acquired image of the workpiece 20 has desired image characteristics. The memory portion 140 may also store inspection result data, further may store data usable to operate the machine vision inspection system 100 to perform various inspection and measurement operations on the acquired images (e.g., implemented, in part, as video tools), either manually or automatically, and to output the results through the input/output interface 130. The memory portion 140 may also contain data defining a graphical user interface operable through the input/output interface 130.

The signal lines or busses 221, 231 and 241 of the stage light 220, the co-axial light 230, and the surface light 240, respectively, are all connected to the input/output interface 130. The signal line 262 from the camera system 260 and the signal line 296 from the controllable motor 294 are connected to the input/output interface 130. In addition to carrying image data, the signal line 262 may carry a signal from the controller 125 that initiates image acquisition.

One or more display devices 136 and one or more input devices 138 can also be connected to the input/output interface 130. The display devices 136 and input devices 138 can be used to display a user interface, which may include various graphical user interface (GUI) features that are usable to perform inspection operations, and/or to create and/or modify part programs, to view the images captured by the camera system 260, and/or to directly control the vision system components portion 200. In a fully automated system having a predefined part program (or workpiece program), the display devices 136 and/or the input devices 138 may be omitted.

In various exemplary embodiments, when a user utilizes the machine vision inspection system 100 to create a part program for the workpiece 20, the user generates part program instructions either by explicitly coding the instructions automatically, semi-automatically, or manually, using a workpiece programming language, or by generating the instructions by operating the machine vision inspection system 100 in a learn mode to provide a desired image acquisition training sequence. For example a training sequence may comprise positioning a workpiece feature in the field of view (FOV), setting light levels, focusing or autofocusing, acquiring an image, and providing an inspection training sequence applied to the image (e.g., using video tools). The learn mode operates such that the sequence(s) are captured and converted to corresponding part program instructions. These instructions, when the part program is executed, will cause the machine vision inspection system to reproduce the trained image acquisition and inspection operation to automatically inspect a workpiece or workpieces matching the workpiece used when creating the part program.

These analysis and inspection methods that are used to inspect features in a workpiece image are typically embodied in various video tools included in the video tool portion 143 of the memory 140, including the autofocus tools 143fb and 143fc. Many known video tools, or "tools" for short, are included in commercially available machine vision inspection systems, such as the QUICK VISION® series of vision systems and the associated QVPAK® software, discussed above.

As outlined previously and described in more detail below with respect to FIG. 4, autofocus tools such as tools 143fb and 143fc typically acquire a series of images and develop focus curves as part of a process for determining a "best focus" position. By utilizing the methods of the present invention which determine refined lighting parameters (e.g., such as are utilized by the lighting optimized focus tools 143fc), images that provide focus curves with higher peak values and greater potential for determining a more accurate "best focus" position can be produced.

Figure 3:
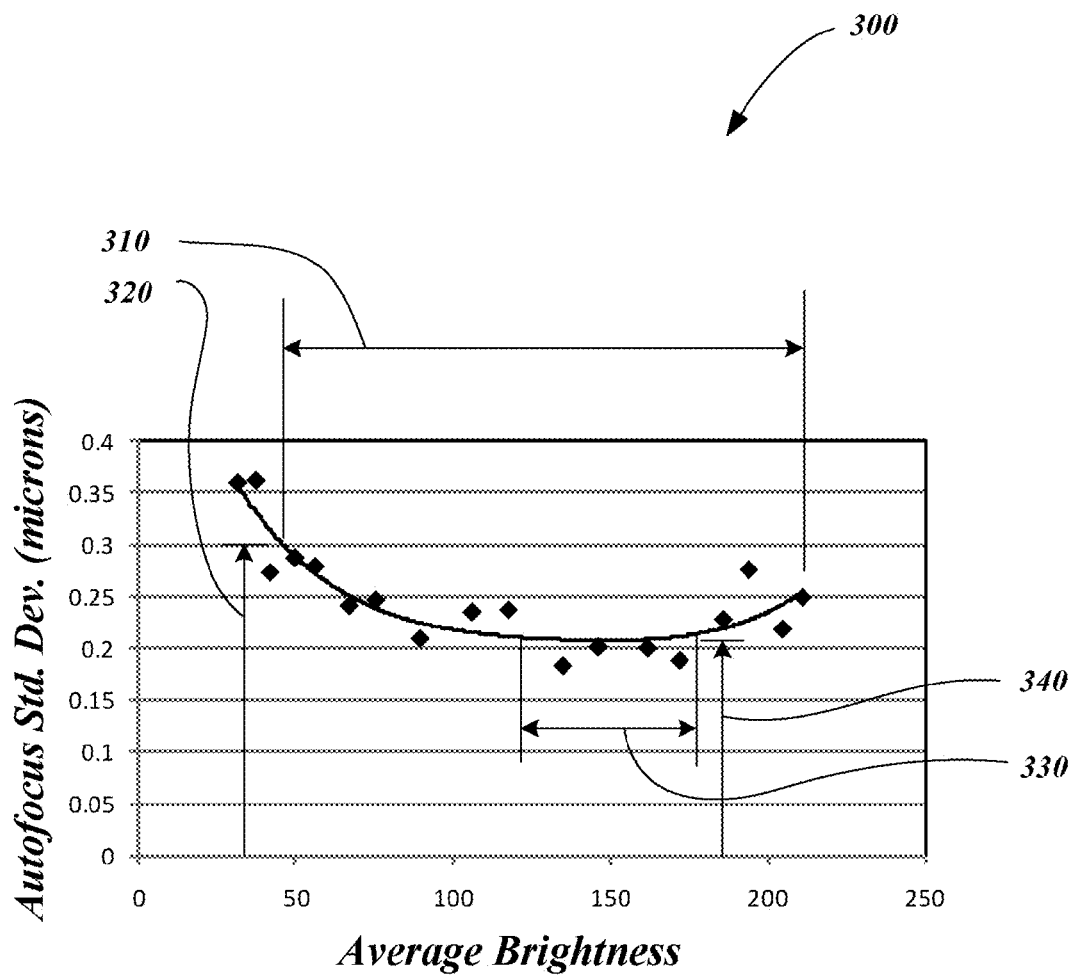
FIG. 3 is a graph indicating representative autofocus repeatability in relation to light level, for a workpiece surface in a precision machine vision inspection system.

FIG. 3 shows a graph 300 illustrating representative autofocus repeatability in relation to light level, for a workpiece surface in a precision machine vision inspection system. In particular, the data shown in the graph 300 were obtained using 2.5× magnification and a 2500 pixel region of interest on a machined metal surface using a co-axial light source. Each "repeatability" data point is the standard deviation of 100 Z-height samples obtained by running an autofocus tool 100 times using a light setting that provides the indicated average brightness for the 2500 pixel region of interest, in a reasonably well focused image. As shown in FIG. 3, there is a relatively broad lighting range 310 where a good level of repeatability may be obtained in the corresponding repeatability range 320 (e.g., better than 0.3 microns). Typical prior art autofocus methods have provided lighting within a reasonable range (e.g., the broad range 310) by qualitative user light setting or by a user implementing lighting adjustment tools which operate independently of other video tools. The broad range 310 generally corresponds to an image that a typical user would judge (e.g., as observed on a monitor) to be not excessively dark and/or excessively saturated (overexposed). Outside of the broad range 310, the image becomes increasingly uniformly dark or light, contrast becomes lower, and repeatability degrades further.

It will be appreciated that a necessary condition for reliably obtaining the best autofocus accuracy is to obtain the best autofocus repeatability. FIG. 3 shows there is an optimized lighting range 330 where the best level of repeatability is be obtained in the corresponding best repeatability range 340 (e.g., better than approximately 0.2 microns). It should be appreciated that qualitative user evaluation cannot generally distinguish lighting in the optimized light range 330 from other lighting conditions that may be included in the broad range 310. Furthermore, the sensitivity of quantitative independent light setting tools to even small amounts of defocus in the image they use for lighting determination has not been appreciated, as described in greater detail below. Therefore, prior art autofocus tools have not reliably enforced lighting within an optimized lighting range 330 that corresponds to the best level of autofocus repeatability 340, and the best levels of autofocus repeatability and accuracy have not been reliably obtained.

Lighting that provides good repeatability is a necessary, but not sufficient, condition for obtaining the best autofocus accuracy. It should be appreciated that lighting may also affect autofocus accuracy in a way that is not strongly reflected in autofocus repeatability. For example, because the appearance of pixels corresponding to inherently very dark or very bright (saturated) surface portions becomes relatively insensitive to focus, the corresponding surface portions lose influence in the contrast curve. Thus, the accuracy of the focus curve and the resulting focus peak may degrade due to the reduced influence of various over- or under-exposed surface portions within the region of interest. However, Z-height errors due to this effect may be repeatable for a given light level, so repeatability is a necessary, but not sufficient, condition related to obtaining the best autofocus accuracy. For this reason, it is also desirable to find a lighting level within the optimized lighting range 330 that further insures that over- and under-exposed pixels are minimized to an insignificant level (or eliminated), so that all regions within the region of interest make the expected varying contribution to the focus metric at various Z-heights. However, it should be appreciated that for a given lighting level, some pixels may saturate in a well-focused image, while they may not saturate in a slightly defocused image because their light is averaged with that of adjacent pixels, due to blur. Thus, in order to obtain the best possible autofocus accuracy, an autofocus tool according to this invention enforces that a refined light setting is quantitatively established based on an initial image that is quantitatively well-focused using an initial light setting, followed by a set of quantitative autofocus operations that are used to establish a best focus Z-height based on images acquired using that refined light setting. Some related considerations are described in greater detail below with reference to FIGS. 4 and 5.

Figure 4:
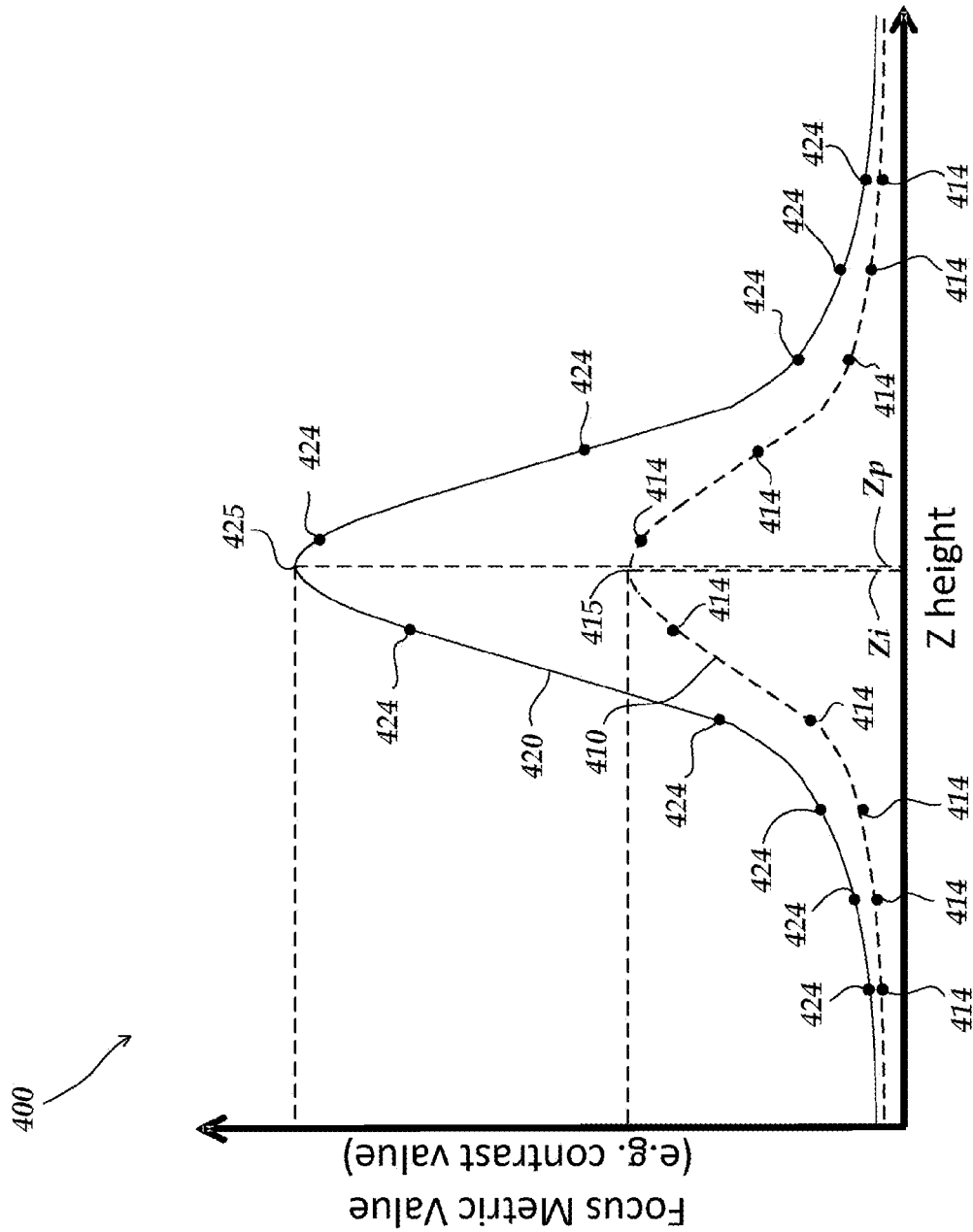
FIG. 4 is a graph illustrating a representative initial lighting focus curve and a representative refined lighting focus curve.

FIG. 4 is a graph 400 illustrating a representative initial lighting focus curve 410 and a representative refined lighting focus curve 420, based on the focus curve data points 414 and 424, respectively. Individual focus curves may be established according to known methods, as previously outlined. Briefly, in one exemplary method, the camera moves through a range of positions or Z-heights along a Z-axis (the focusing axis) and captures an image at each position. For each captured image, a focus metric value is calculated based on the image and that value becomes a data point (e.g., one of the data points 414 or 424 in the graph 400) related to the corresponding Z-height at the time that the image was captured. This results in focus curve data, which may be referred to simply as a "focus curve" or "autofocus curve". The peak of the focus curve (e.g., the focus peak 425, or the focus peak 415), which corresponds to the best focus position along the Z-axis (and the Z-height of the region of interest on the workpiece) may be found by fitting a curve to the focus curve data (at least in the vicinity of the peak) and estimating the peak of the fitted curve. Various known focus metrics may be used. In one example, the focus metric value may be calculated as:

$$M_{F1} = \sum_{i=1}^{n} ((A_i - B_i)^2 + (A_i - C_i)^2 + (D_i - B_i)^2 + (D_i - C_i)^2) \quad (1)$$

where $A_i$, $B_i$, $C_i$, and $D_i$ are the gray levels or intensities for the "ith" group of four nearest-neighbor pixels in the autofocus region of interest, and the summation for i=1 to n accounts for all "n" groups of four nearest neighbors in the autofocus region of interest. In various embodiments the focus metric values or curve may be normalized, if desired. In one embodiment, the focus metric values or curve may be normalized by the average grayscale value or average of squared grayscale values of the image pixels in the region of interest. However, the foregoing metric is exemplary only, and not limiting. More generally, any suitable now-known or later-developed metric that is indicative of the global region of interest focus or contrast may be used.

As outlined previously, autofocus repeatability and accuracy may be optimized by an appropriate light level for an image. Furthermore, an appropriate level (e.g., a light level that reduces the number of saturated pixels to an insignificant level) is best established in a well-focused image. Thus, in order to obtain the best possible autofocus accuracy, an autofocus tool according to this invention enforces that a refined light setting is quantitatively established based on an initial image that is quantitatively well-focused using an initial light setting, followed by a set of quantitative autofocus operations that are used to establish a best focus Z-height based on images acquired using that refined light setting. Interpreting the example shown in FIG. 4 according to this method, the initial light setting is used to acquire the images corresponding to the data points 414 of the initial focus curve 410. Then the peak 415 of the initial focus curve, corresponding to the Z-height Zi, is quantitatively determined (e.g., by locating the peak 415 of the focus curve 410, which is fit to the data points 414). Then the refined light setting is quantitatively established based on an initial image that is focused corresponding to the quantitatively determine Z-height Zi. In some embodiments, the initial image that is used to quantitatively establish the refined light setting is one of a plurality of differently lit images acquired at the Z-height Zi. In another embodiment, the refined light setting is quantitatively established based on a single image acquired at the Z-height Zi. Various methods of established the refined light setting are described below, with reference to FIG. 5. In any case, once the refined light setting is established, a set of autofocus operations are used to acquired the data points 424 and establish the best focus Z-height Zp (e.g., as outlined previously) based on images acquired using that refined light setting. In general, for reasons previously discussed in relation to FIG. 3, the initial light setting is not optimal for providing the best autofocus repeatability and accuracy. Thus, as shown in FIG. 4, Zi and Zp are generally not identical. However, if a reasonable initial lighting level (e.g., within the range 310 shown in FIG. 3) is established by prior art methods, the initial focus curve data 414 will general yield a focus height Zi that provides an image that is sufficiently well focused to establish an optimal refined light setting (e.g., potential saturated pixels will not be obscured by image blur).

The initial light level can be regarded as being non-optimal (e.g., somewhat under- or over-exposed, leading to reduced image contrast), whereas the refined lighting level is specifically determined such that it is approximately optimal (e.g., corresponding to the best level within the optimized lighting range 330, shown in FIG. 3) for maximizing image contrast and related focus metrics, as described in greater detail below. Therefore, as illustrated in FIG. 4, the refined light setting provides a refined lighting focus curve 420 that has higher focus metric values and a higher peak 425 than the initial lighting focus curve 410. This can be interpreted as the data points 424 and the refined lighting focus curve 420 providing a better signal to noise ratio and better curve fitting than the initial lighting focus curve 410, which leads to improved autofocus accuracy and repeatability. In particular, based on the operations outlined above, the signal to noise ratio of the data points 424 and the refined lighting focus curve 420 is reliably approximately optimal, leading to reliably obtaining the best possible autofocus repeatability (e.g., corresponding to the range of the best level of repeatability 340, shown in FIG. 3) and the best autofocus accuracy.

It should be appreciated that the number of data points shown for the focus curves 410 and 420 is exemplary only and not limiting. Either curve may be determined from greater or fewer data points, corresponding to more widely spaced or more closely spaced image Z-heights, respectively. In one embodiment, the initial focus curve (e.g., focus curve 410) is determined with data points at a first relatively wide spacing, to speed up the related subset of autofocus operations, whereas once the refined lighting level is determined, the refined lighting focus curve (e.g., focus curve 420) is determined with data points at a second relatively close spacing, to support more accurate curve fitting and more accurate determination of the final autofocus Z-height (e.g., Zp). In various implementations or applications, the final autofocus Z-height that is determined using the refined light setting is either used to determine a Z-height inspection dimension for a workpiece surface in the region of interest, or to position the camera at the best focus position along the Z-axis to maximize the sharpness of features (e.g., an edge in the image plane prior to edge detection), or both. Various considerations related to establishing refined light settings are described below with reference to FIG. 5.

Figure 5:
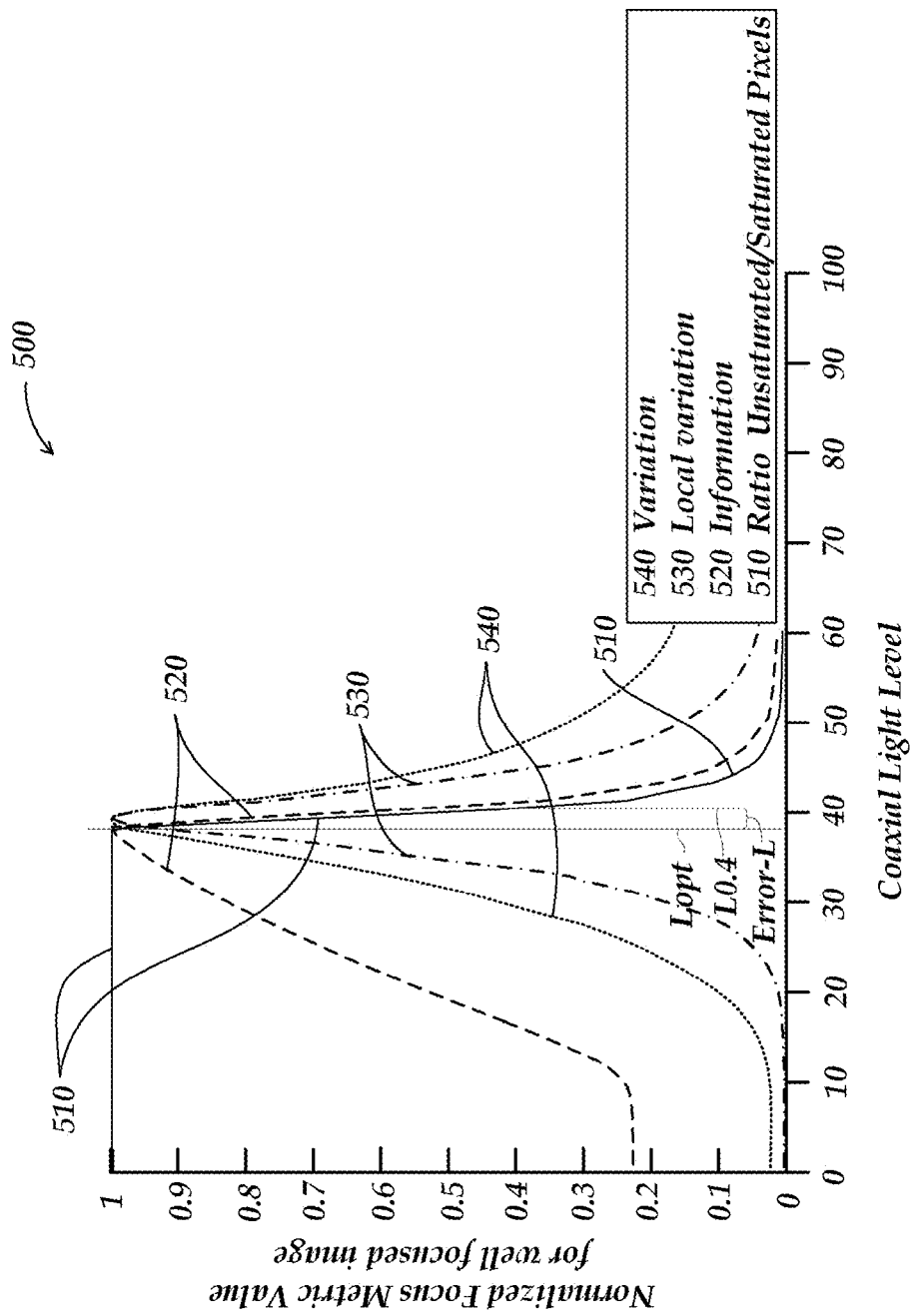
FIG. 5 is a graph illustrating representative lighting level sensitivity data and/or curves for focus-related metrics such as pixel brightness variation levels, information, and unsaturated pixel ratios relative to a lighting level.

FIG. 5 is a graph 500 illustrating representative experimentally-determined lighting level sensitivity curves 510-540. In particular, the lighting level sensitivity curves 510-540 indicate normalized values of contrast-related metrics relative to the power or brightness setting of a co-axial (through the objective lens) lighting channel used to illuminate a region of interest (e.g., as defined by an autofocus tool) on a workpiece during the acquisition of a well-focused images that are used for determining the values of the metrics.

It will be appreciated that focus metrics are generally contrast metrics. The lighting level sensitivity curves 520-540 illustrate the sensitivity to light level for a selection of contrast metrics, which may be considered both contrast-related metrics and focus metrics (e.g., suitable for establishing the focus curve 420 shown in FIG. 4). However, the lighting sensitivity curve 510 illustrates the sensitivity to light level of the ratio of unsaturated pixels to saturated pixels in the region of interest. This ratio is not suitable for use in establishing a focus curve. However, it is considered a contrast-related metric, in that image contrast is affected by lighting as well as by focus. For example, saturated pixels tend to indicate an overexposed image, and overexposed images generally have poorer contrast than properly exposed images. Analysis of saturated pixels may therefore be used to establish refined light settings in some embodiments. Considerations related to the lighting sensitivity curve 510 and establishing refined light setting are described in greater detail further below. Similarly, at levels below saturation, pixel brightness metrics (e.g., the brightness of the brightest pixel or the average brightness on several brightest pixels, or the number of the pixels above a brightness threshold, or the like) may also be considered contrast-related metrics.

Regarding the contrast or focus metric lighting sensitivity curves 520-540, since all metric values on the curves are established based on well focused images (corresponding to a focus peak), the height of these curves at each light level indicates the maximum height of the focus curve peak that can be achieved using that light level. As previously indicated with reference to FIG. 4, a higher focus curve peak may be associated with determining a Z-height and/or best focus position with the better accuracy and repeatability. As shown in FIG. 4, the light level that maximizes each of the focus metrics corresponding to the curves 520-540 is in the range of approximately 38-41. Therefore, a refined light setting in approximately this same range would reliably provide the approximately the highest possible focus curve peak and, therefore, the best autofocus repeatability and accuracy. It may be seen in FIG. 4 that for this example if the light setting varies by only a small amount (e.g., by 10% or approximately 4 setting increments out of 100) that the maximum possible focus curve peak (corresponding to the lighting sensitivity curve height at each light setting) drops significantly (e.g., by 40-60%). In contrast to the present invention, previous autofocus tools and methods have not reliably recognized or overcome this lighting sensitivity, to provide the best possible lighting which provides the highest focus curve peak and the best possible autofocus repeatability and accuracy. To summarize, in some embodiments, for reliably providing the refined lighting level that supports near-optimum autofocus accuracy, a quantitatively well focused image is required and used for establishing a refined lighting level such that it approximately maximizes a contrast-related metric that is a contrast metric and/or a focus metric. In some embodiments, it is desirable to choose a refined lighting level such that it also avoids saturating image pixels under expected variations in workpiece reflectance and/or lighting repeatability, or the like. Related considerations are discussed further below.

It will be appreciated that there may be many ways to mathematically define contrast. For example, for the particular contrast metrics curves shown in FIG. 5, the pixel brightness information data curve 520 is based on:

$$\text{Value} = -\sum_{i=0}^{255}\left(\frac{\text{\# Pixels with brightness } i}{\text{Total Pixels}}\right) * \log\left(\frac{\text{\# Pixels with brightness } i}{\text{Total Pixels}}\right) \quad (2)$$

The pixel brightness local variation data curve 530 is based on:

$$\text{Value} = \sum_{i=1}^{n}\sum_{k=1}^{9}(X_k - Xavg)^2 \quad (3)$$

where $X_k$ is the gray level or intensity for the "kth" pixel of the "ith" group of nine nearest-neighbor pixels in the autofocus region of interest, Xavg is the average of that group, and the summation for i=1 to n accounts for all "n" groups of nine nearest neighbors in the autofocus region of interest.

The pixel brightness global variation data curve 540 is based on:

$$\text{Value} = \sum_{p=1}^{n}(X_p - XavgROI)^2 \quad (4)$$

where $X_p$ is the gray level or intensity for the "pth" pixel in the autofocus region of interest, XavgROI is the average gray level of the pixels in the autofocus region of interest, and the summation for p=1 to n accounts for all "n" pixels in the autofocus region of interest.

In addition to the foregoing, other possible contrast measures include: the pixel brightness range (max-min); the square of the sum over the local differences; the sum of the square of the first (or second) spatial derivatives; and others (e.g., see EP Krotkov, Focusing, Int. J. Comp. Vis., 1(3) 223-237, 1987). In certain implementations, contrast measures can be applied over the entire region of interest, or applied to sub-windows to create local measures of contrast that can be combined (averaged together) to form a contrast measure for the entire region of interest. Different measures may be more desirable for specific applications. In general, in certain implementations measures based on local image variation (e.g., local variation data curve 530 of FIG. 5) are considered to be better suited for certain tasks because many image features are local in nature.

Regarding the unsaturated pixel ratio lighting sensitivity curve 510, as shown in FIG. 5 it exhibits a transition point at a light level Lopt (at a light level of approximately 38), where it decreases from a value of 1.0 with increasing light level (corresponding to an increasing number of saturated pixels). It may be seen in FIG. 4 that the light level Lopt approximately coincides with the lower limit of the light level range that maximizes each of the focus metrics corresponding to the curves 520-540. This is not surprising in that for unsaturated pixels increasing the light level generally increases both the brightest and the darkest image pixels proportionately, such that the difference between them increases proportionately. Thus, contrast metrics which respond to the brightness difference between pixels tend to increase along with brightness. However, as the light level becomes too bright, more and more pixels saturate. Since the difference or contrast between more and more of the brighter pixels decreases (due to the fixed saturation value), contrast metrics for a region of interest begin to decrease as an increasing number of pixels saturate. Thus, in a reasonably well focused image, the light setting that provides the highest focus metric value is typically near to the light setting at which saturation begins to occur. (Although, it is worth noting that this linear model may not necessarily be sufficient to achieve optimum lighting when multiple lighting channels are used to illuminate a workpiece.)

It may be seen in FIG. 4 that for this example if the light setting varies from Lopt by only a small amount shown as Error-L (e.g., by just 5% or approximately 2 setting increments out of 100), to a light level L0.4, that the percentage of unsaturated pixels drops significantly to approximately 40%, indicating that 60% of the pixels in the region of interest are saturated. In contrast to the present invention, previous autofocus tools and methods have not reliably recognized or overcome this lighting sensitivity, to provide the best possible autofocus repeatability and accuracy. In addition to reducing the focus curve peak height and autofocus repeatability, as previously indicated the effective loss of any significant percentage of the image due to saturation may cause very significant autofocus errors in that the remaining focus-sensitive pixels may represent workpiece surface portions which are not at the average height of the region of interest as a whole. As previously indicated, some pixels may saturate in a well-focused image, while they may not saturate in a slightly defocused image because their light is averaged with that of adjacent pixels, due to blur. Thus, in some embodiments, for reliably providing the refined lighting level that supports near-optimum autofocus accuracy, a quantitatively well focused image is required and used for establishing the refined lighting level such that it is approximately as bright as possible, while still insuring that saturated pixels are minimized to a desired level, or prevented. In one embodiment, such a refined lighting level may be determined based on a contrast-related metric that is responsive to pixel brightness (a pixel brightness metric) and/or to the number or proportion of saturated pixels (a saturated pixel metric) in the region of interest in a quantitatively well focused image (e.g., determined as a lighting level that is proximate to a transition point where a ratio of unsaturated pixel to total pixels begins to decrease with increasing light level).

As previously outlined, in some embodiments, it is desirable to choose a refined lighting level such that it limits or prevents saturated image pixels not only for a well focused image of a current workpiece region of interest, but also under expected variations in workpiece reflectance and/or lighting repeatability, or the like, for a future well focused image of a corresponding workpiece region of interest on a similar workpiece (e.g., when inspecting multiple similar workpieces using a part program). In such a case, it may be desirable to select a refined lighting level that is set slightly below the lighting level that maximizes a contrast metric or a focus metric in a quantitatively well focused image, and/or slightly below the lighting level "transition point" where saturated pixels begin to appear. Such an embodiment may be particularly useful when setting a refined lighting level for future use in a part program, for example. Various part program implementations of this invention are described further below. In one example embodiment it may be desirable to set the refined lighting level below the level that provides the maximum possible value of a contrast metric or focus metric, for example, at most 95% of its maximum possible value, or at most 90%, or less in some embodiments. However, in various embodiments, it is desirable that the metric attains at least 60% of its maximum possible value as a function of light level to provide sufficient accuracy and repeatability in various applications, according to principles outlined above. However, these particular values are exemplary only, and not limiting. It will be appreciated that in some embodiments, determining a refined light level as outlined above may comprise varying the light levels to obtain a plurality of quantitatively well focused images at respective lighting levels and determining lighting sensitivity data (e.g., data similar to a lighting sensitivity curve, or a portion thereof, as shown in FIG. 5 and described above) for a contrast-related metric, and determining the refined lighting level based on the lighting sensitivity data. In another embodiment, a refined light level that satisfies the general inventive principles outlined above may be determined based on a least one quantitatively well focused image acquired with a known light level. For example, if the linear lighting model outlined above is applicable, a quantitatively well focused image may be acquired using a relatively low light level. Then, the brightest pixel(s) in the region of interest may be identified in that image. Then, assuming a linear relationship between light level settings and image pixel brightness, by extrapolating image characteristics refined light level may be identified where a pixel brightness metric or a pixel saturation metric indicates that a number of the brightest pixels (e.g., 1, 10, or 50 pixels, or 1% or 2% of the pixels in the ROI, or the like) reach at least 90%, or 95%, or 100% of saturation value, or another level consistent with principles outlined herein. In another embodiment, a plurality (e.g., two) quantitatively well focused images may be acquired using respective light levels. Then, the change in brightness of the brightest pixel(s) in the region of interest, or the change in a contrast or focus metric may be determined between the images. Then, assuming a linear relationship between light level settings and image pixel brightness, or assuming a predetermined shape for the lighting sensitivity curve of the contrast or focus metrics, the refined light level may selected based on extrapolating image characteristics to a refined light level where a pixel brightness metric or a pixel saturation metric indicates that number of the brightest pixels reach at least 90%, or 95%, or 100% of saturation value, or another level consistent with principles outlined herein, or the contrast or focus metric achieves at least a desired percentage of its maximum value as a function of light level (e.g., 60%, or 75%, or 80%, or more in various embodiments), or another level consistent with principles outlined above. Various methods of extrapolation to a desired light setting and/or combination of lights settings based on a limited number of actual images are taught in the previously incorporated '180 and '863 patents, and such methods may be adapted in a manner consistent with the principles disclosed for the present invention.

The foregoing metrics and associated limits or target levels may be regarded as corresponding to refined light control parameters that provide sufficiently optimal lighting in various embodiments. However, it will be appreciated that the foregoing metrics and associated limits or target levels are exemplary only, and not limiting. Particular metrics and/or limiting or target values may be appropriated for particular applications, workpieces, or regions of interest, as may be determined based on experience. In addition, it will be apparent that a combination of metrics such as those outlined above may be used in combination, in some embodiments. For example, in one embodiment it may be required that during run mode the refined light control parameters satisfy the condition that a contrast metric for a quantitatively well focused image attains a minimum value corresponding to at least 60% of a maximum value (e.g., the maximum value may established on lighting sensitivity data obtained during learn mode), and that a pixel brightness metric or a saturated pixel metric indicate that no pixels are saturated.

It will be appreciated that in some embodiments various operations outlined above may be implemented in a learn mode of operations (e.g., when determining the operations and parameters to be recorded and used in a part program). In other embodiments, various operations outlined above may be implemented in a run mode of operations (e.g., when automatically executing a part program). Various implementations are described further below, with reference to FIGS. 7-11.

Figures 6A, 6B:
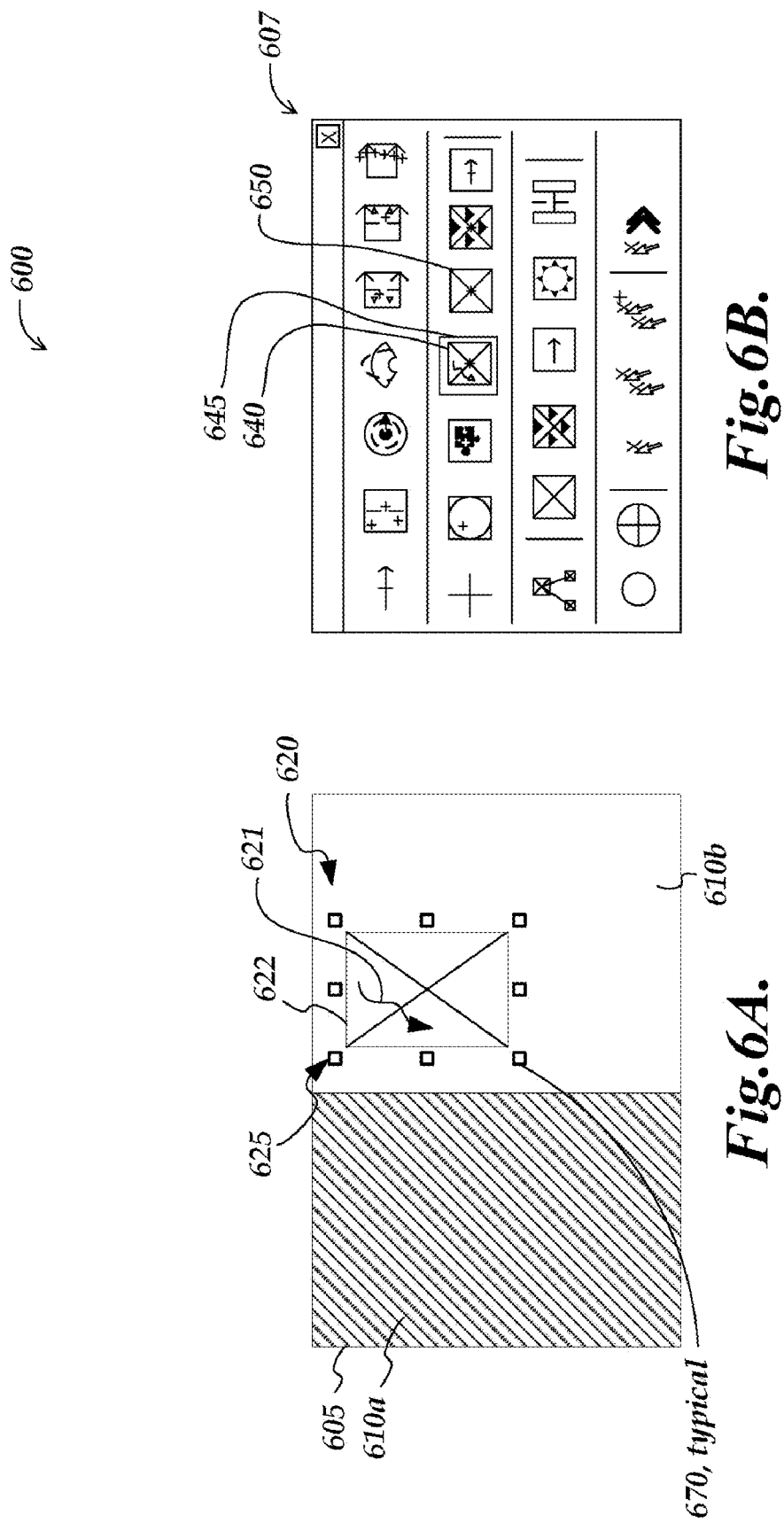
FIGS. 6A and 6B are diagrams illustrating various features of one embodiment of an autofocus video tool user interface.

FIGS. 6A and 6B are diagrams illustrating various features of one embodiment of a user interface 600 that includes a refined lighting autofocus tool user interface 620 (the appearance of which may also be referred to as the refined lighting autofocus tool user interface widget 620). FIG. 6A shows a field of view 605 including two workpiece surfaces 610a and 610b, and the refined lighting autofocus tool user interface 620, including a lighting symbol mode indicator 621 that indicates the autofocus tool user interface 620 operates in a refined lighting autofocus mode according to this invention, and a region of interest or region of interest indicator 622 that is defined while the refined lighting autofocus tool mode is active. It will be appreciated that in some vision systems, a refined lighting autofocus tool, mode, or method disclosed herein may be provided along with known or conventional autofocus tools, modes or methods. Thus, the lighting symbol mode indicator 621 distinguishes the refined lighting autofocus mode of operation from other modes of autofocus operation. Various aspects of the operation of the refined lighting autofocus tool and its user interface 620 that are not described in detail herein may operate according to known methods in commercial systems, and/or otherwise as described herein. In the view shown in FIG. 6A, the user interface region of interest 622 has been selected for editing. When the region of interest 622 is selected for editing, a set of size/location editing handles 625 (including individual handles such as handle 627 which may be controlled by dragging) may be displayed along the corners and sides, as shown. The refined lighting autofocus tool or mode (e.g., as implemented by the user interface 620) enforces certain combinations of operations according to principles outlined above. In particular, the refined lighting autofocus tool or mode enforces that a refined light setting is quantitatively established based on an initial image that is quantitatively well-focused using an initial light setting, followed by a set of quantitative autofocus operations that are used to establish a best focus Z-height based on images acquired using that refined light setting.

FIG. 6B illustrates one embodiment of a tool selection bar 607, including a refined lighting autofocus tool-type activation button 640. FIG. 6B shows a user interface configuration wherein the tool selection bar 607 indicates that the refined lighting autofocus tool or mode is active via an "active" box 645 around the refined lighting autofocus tool or mode button 640, and the other autofocus tool/mode buttons are set to inactive (there is no "active" box around the other tool/mode buttons). This indicates that the current autofocus tool mode is the refined lighting autofocus tool mode. In various embodiments, if the user were to "press" one of the other tool/mode buttons (e.g., the non-refined lighting or conventional autofocus tool or mode button 650), the pressed tool and/or mode would become active and the operations and display elements associated with editing the individual region of interest (indicator) 622 (shown in FIG. 6A), and the operations of the refined lighting autofocus tool or mode would then be completed and/or disabled. In some embodiments, the state of the tool selection bar 607 in FIG. 6B may correspond to the state of the user interface displayed in FIG. 6A, in that if the region of interest (indicator) 622 is selected or active, the refined lighting autofocus tool or mode may be made active in association with the tool 620 and other tool/mode buttons may become inactive, regardless of their previous state. This may also be the behavior associated with any other tool when its region of interest (indicator) is selected in the field of view 605.

In one embodiment, a tool mode determining operation may be provided that determines whether one or more instances of the refined lighting autofocus tool 620 is configured to operate according to particular implementation, such as a learn-mode governed implementation, or a run-mode refinement implementation, or a conditional run-mode refinement implementation, or a run-mode originated implementation, each of which is described in greater detail below. In one embodiment, the particular implementation of the refined lighting autofocus tool 620 may be set by a user using a user interface features such as a configuration menu window or the like that sets operating parameters for the autofocus tools or modes in general, and/or for the refined lighting autofocus tool or mode in particular.

Figure 7A:
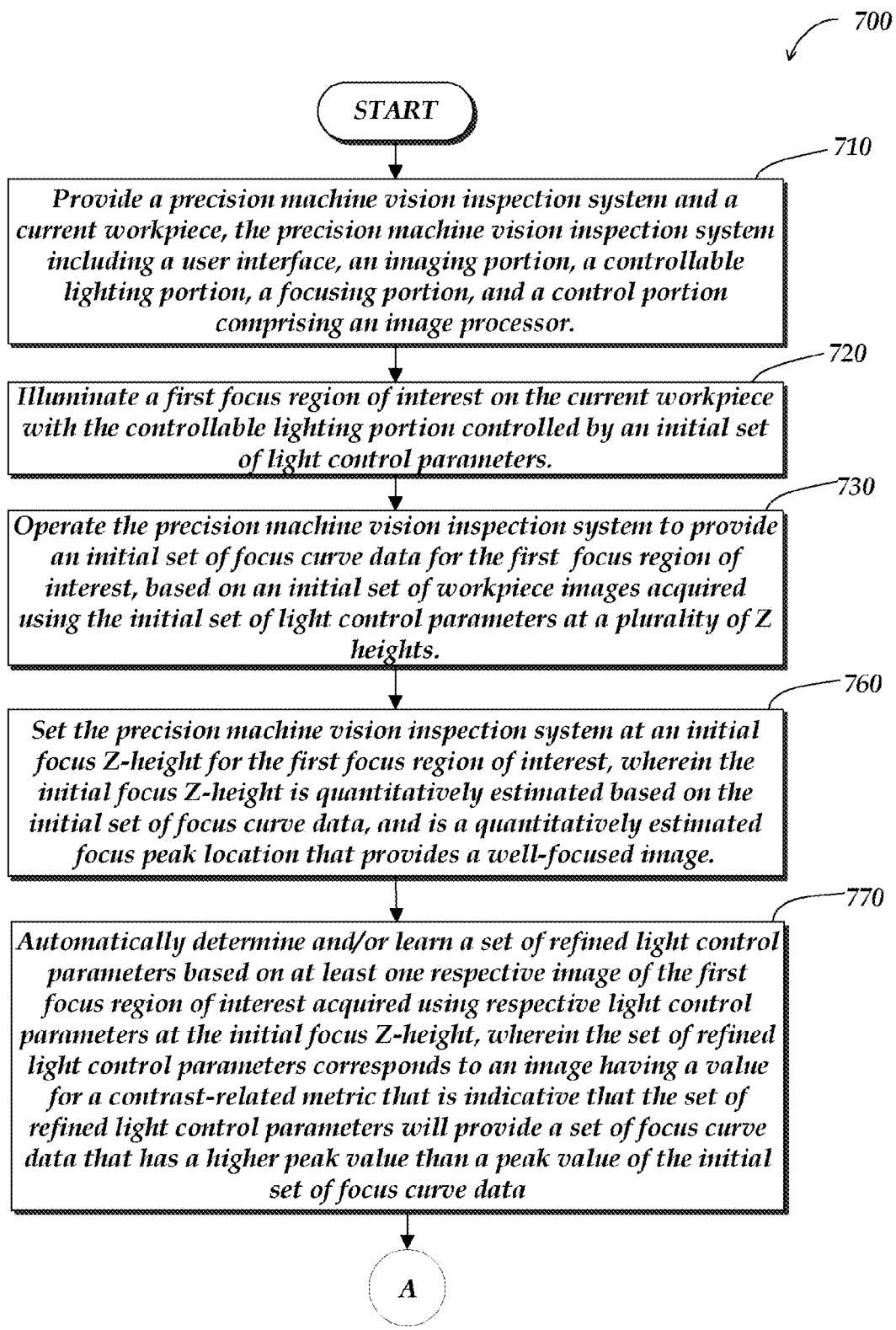
FIGS. 7A and 7B are flow diagrams illustrating a first exemplary routine for implementing refined lighting autofocus operations during learn mode or run mode.
Figure 7B:
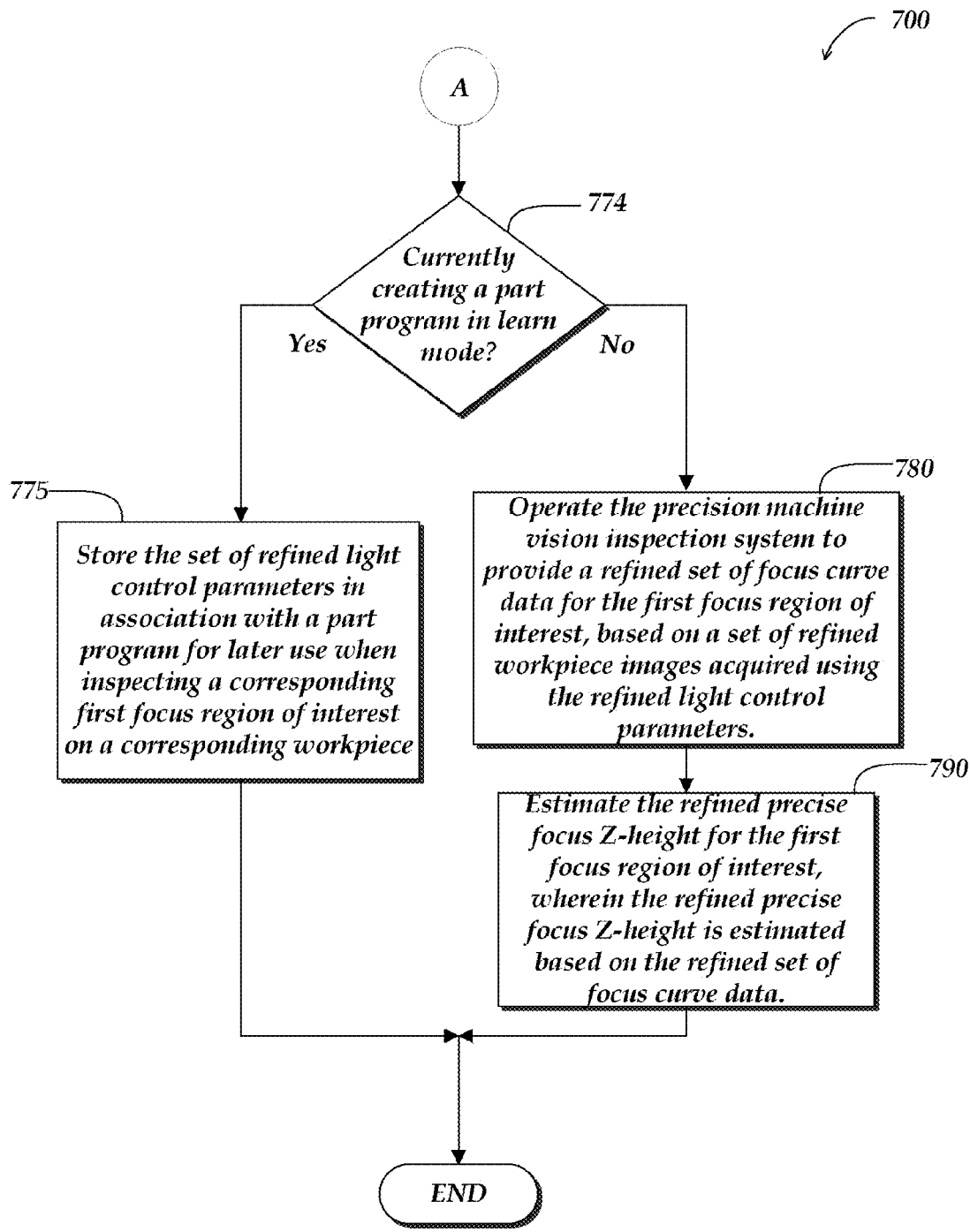

FIGS. 7A and 7B are flow diagrams illustrating a first exemplary routine 700 for implementing refined lighting autofocus operations during learn mode or run mode. As shown in FIG. 7A, at a block 710 a precision machine vision inspection system and a current workpiece are provided. The precision machine vision inspection system may include a user interface, an imaging portion, a controllable lighting portion, a focusing portion, and a control portion comprising an image processor, for example.

At a block 720, a first focus region of interest is illuminated on the current workpiece with the controllable lighting portion controlled by an initial set of light control parameters (e.g., as set by a user or by an independent light adjustment tool). At a block 730, the precision machine vision inspection system is operated to provide an initial set of focus curve data for the first focus region of interest, based on an initial set of workpiece images acquired using the set of light control parameters at a plurality of Z-heights. At a block 760, the precision machine vision inspection system is set at an initial focus Z-height for the first focus region of interest, wherein the initial focus Z-height is quantitatively estimated based on the initial set of focus curve data, and is a quantitatively estimated focus peak location that provides a well-focused image, as a basis for providing refined optimized lighting according to principles previously outlined with reference to FIGS. 3-5. At a block 770, a set of refined light control parameters are automatically determined and/or learned based on at least one respective image of the first focus region of interest acquired using respective light control parameters at the initial focus Z-height. Although a single image is sufficient for some situations as outlined previously, determining the set of refined light control parameters based on a plurality of images that use respective light control parameters may be more robust when a combination of lighting channels is used for illumination, or when workpiece characteristics not unpredictable, or when the highest possible accuracy is required, or the like. In any case, the set of refined light control parameters correspond to an image having a value for a contrast-related metric (e.g., a saturated pixel metric or a contrast metric) that is indicative that the set of refined light control parameters will provide a set of focus curve data that has a higher peak value than a peak value of the initial set of focus curve data. Various considerations related to contrast-related metrics and their use in determining a set of refined light control parameters have been outlined previously (e.g., particularly with reference to FIGS. 4 and 5) and the operations at block 770 may be configured accordingly. The routine then continues to a point A, which continues at a decision block 760 in FIG. 7B.

As shown in FIG. 7B, at the decision block 774 (which continues from point A of FIG. 7A), if the current set of refined lighting autofocus operations is being implementing during learn mode to create a part program (e.g., as in the case of refined lighting autofocus tool operations performed while training the tool during learn mode), then the operations continue to a block 775, where the set of refined light control parameters determined at block 770 are stored in association with the part program for later use when inspecting a corresponding first focus region of interest on a corresponding workpiece (e.g., in the learn-mode governed, or unconditional or conditional run-mode refinement implementations described with reference to FIGS. 8A and 8B). Otherwise, if the current set of refined lighting autofocus operations is not being implementing during learn mode to create a part program at the decision block 774 (e.g., as in the case of refined lighting autofocus tool operations implemented for manual inspection or during an automatic run mode implementation under part program control), then the operations continue to a block 780. At the block 780, the precision machine vision inspection system is operated to provide a refined set of focus curve data for the first focus region of interest, based on a set of refined workpiece images acquired using the set of refined light control parameters determined at block 770. Then at a block 790, the refined precise focus Z-height for the first focus region of interest is quantitatively estimated based on the refined set of focus curve data (e.g., according to previously outlined principles). In some embodiments, the refined precise focus Z-height is recorded as an inspection dimension. In other embodiments, the machine vision inspection system is positioned at the refined precise focus Z-height to obtain an image with the best possible focus in the first region of interest. In one embodiment, an implementation where operation continues to the blocks 780 and 790 may correspond to including refined lighting autofocus tool operations in a part program and initiating that tool during run mode (e.g., without determining a set of refined lighting parameters during learn mode). Such an implementation may be referred to as a run-mode originated implementation. Such an implementation may be suitable when run mode execution time is not critical and/or the lighting channels are constrained to a simple configuration, for example.

Figure 8A:
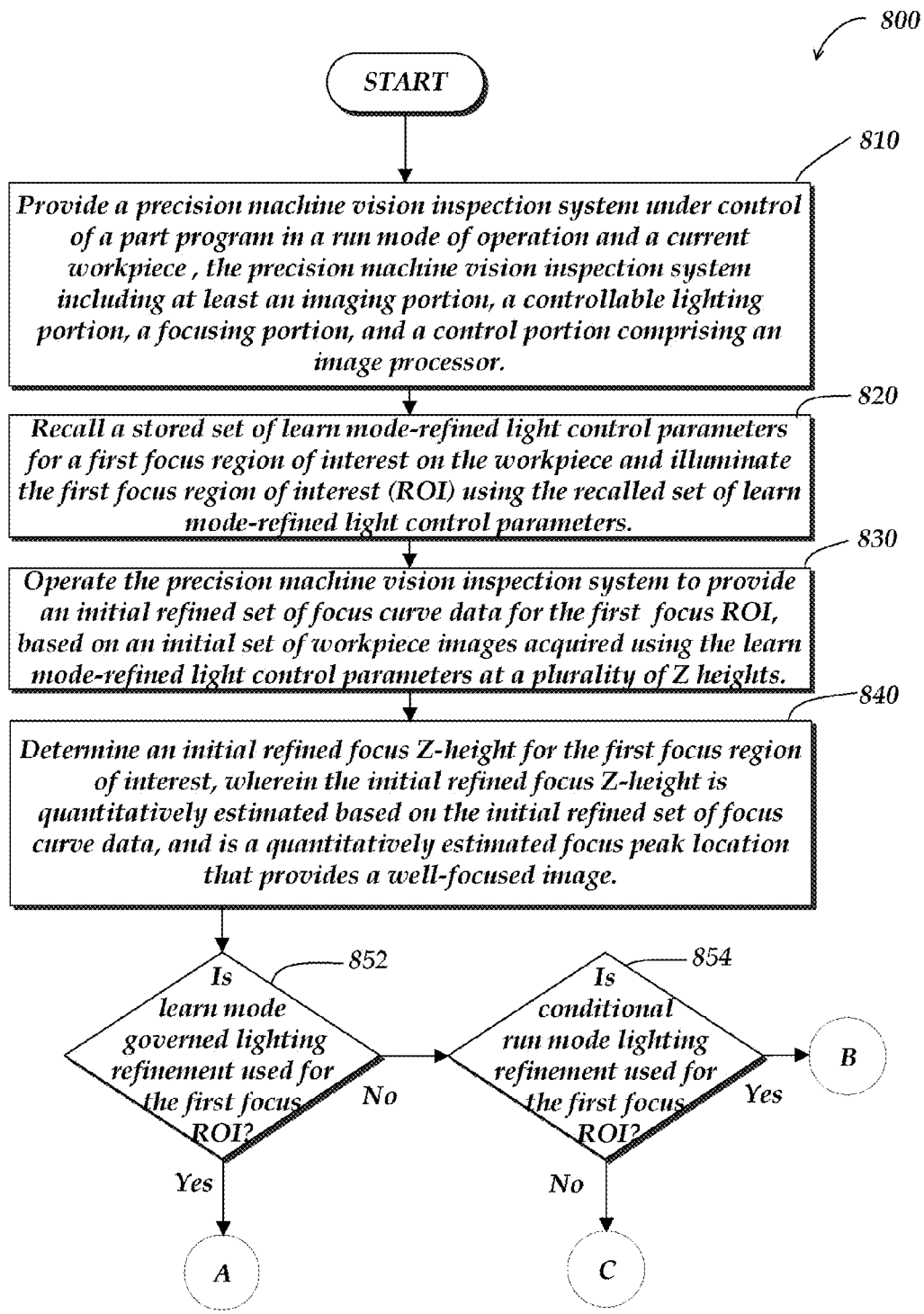
FIGS. 8A and 8B are flow diagrams illustrating a second exemplary routine for implementing various alternative sets of refined lighting autofocus operations during run mode.
Figure 8B:
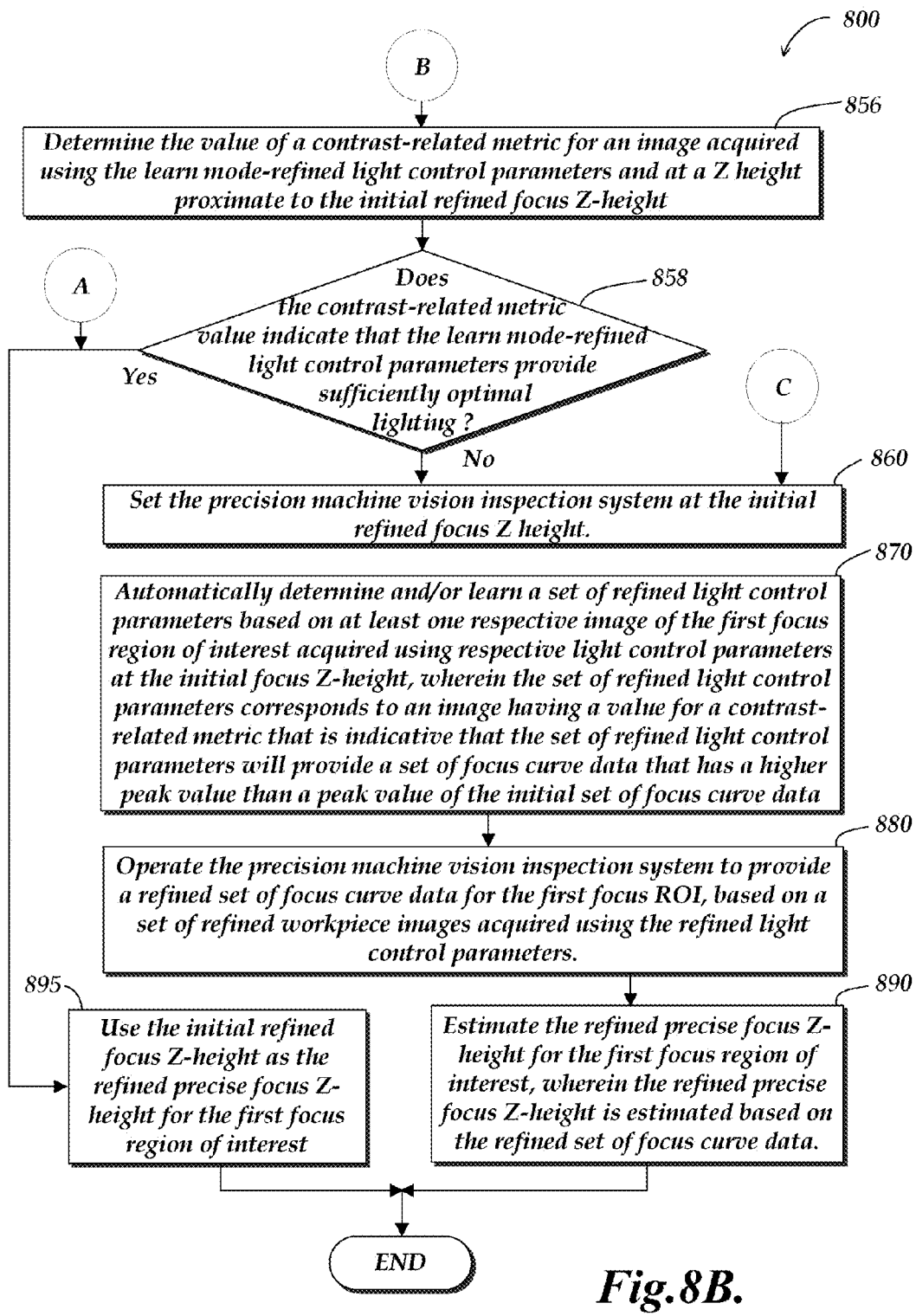

FIGS. 8A and 8B are flow diagrams illustrating a second exemplary routine 800 for implementing various alternative sets of refined lighting autofocus operations during run mode (e.g., under control of a part program). As shown in FIG. 8A, at a block 810 a precision machine vision inspection system is provided under control of a part program in run mode, along with a current workpiece to be inspected. The precision machine vision inspection system may include an imaging portion, a controllable lighting portion, a focusing portion, and a control portion comprising an image processor, for example.

At a block 820, a stored set of learn mode-refined light control parameters is recalled for a first focus region of interest (e.g., as recorded in the part program or an associated memory location in the control portion of the machine vision inspection system) and the corresponding first focus region of interest on the current workpiece is illuminated with the controllable lighting portion using the recalled set of learn mode-refined light control parameters (e.g., learn mode-refined light control parameters as determined and stored at block 775 of FIG. 7B, for example). At a block 830, the precision machine vision inspection system is operated to provide an initial refined set of focus curve data for the first focus region of interest, based on an initial set of workpiece images acquired using the recalled learn mode-refined light control parameters at a plurality of Z-heights. Then, at a block 840, an initial refined focus Z-height is determined for the first focus region of interest, wherein the initial refined focus Z-height is quantitatively estimated based on the initial refined set of focus curve data, and is a quantitatively estimated focus peak location that provides a well-focused image (e.g., according to previously outlined principles).

In the embodiment shown in FIGS. 8A and 8B, the current type of run mode refined lighting autofocus implementation is then determined, as reflected by the decision blocks 852 and 854. In particular, operation continues from block 840 to decision block 852, where if a learn mode governed set of refined lighting autofocus operations is being implemented then the routine continues to a point A, which continues to a block 895 in FIG. 8B, where the initial refined focus Z-height is used as the refined precise focus Z-height for the first focus region of interest. In other words, in a learn mode governed implementation, the set of refined light control parameters determined for the first focus region of interest during learn mode operations are considered to be sufficiently optimum for use in precise autofocus operations for determining a refined precise focus Z-height for a corresponding first focus region of interest on a corresponding workpiece during run mode. It will be appreciated that the learn mode governed implementation may useful when fast run mode execution is desired, and it is determined that surface (or edge) reflectance characteristics are consistent between workpieces, and/or sufficient accuracy will be provided by the learn mode governed implementation. In some embodiments, such a determination may be based on lighting sensitivity data acquired and analyzed during learn mode operations, as outlined previously with reference to FIG. 5. If it is determined at the decision block 852 that a learn mode governed set of refined lighting autofocus operations is not being used for the first focus region of interest, then operation continues to the decision block 854.

At decision block 854 it is determined whether conditional run mode lighting refinement autofocus operations are being implemented. If not, then unconditional run mode lighting refinement autofocus operations are being implemented, and the routine continues to a point C, which unconditionally continues to a block 860 FIG. 8B, where a further run mode refinement of the autofocus lighting parameters is initiated, as described in greater detail below. If it is determined at decision block 854 that conditional run mode lighting refinement autofocus operations are being implemented, then the routine continues to a point B, which continues to blocks 856 and 858 in FIG. 8B, where it is determined whether the value of a contrast-related metric indicates a "condition" where a further run mode refinement of the autofocus lighting parameters is required. In particular, at the block 856 the value of a contrast-related metric (e.g., a saturation or contrast metric as previously outlined with reference to FIG. 5) is determined for an image acquired using the recalled learn mode-refined light control parameters at a Z-height proximate to the initial refined focus Z-height (e.g., as determined at the block 840). In one embodiment, if one of the initial set of workpieces images (as acquired at the block 830) was acquired at a Z-height that is sufficiently close to the initial refined focus Z-height (e.g., within the depth of field of the objective lens of the system), then that image may be used to determine the value of a contrast-related metric at block 856. In another embodiment, the system may be positioned precisely at the initial refined focus Z-height and an image acquired using the recalled learn mode-refined light control parameters, and that image may be used to determine the value of the contrast-related metric at block 856. In any case, operation then proceeds from block 856 to the decision block 858.

At the decision block 858 it is determined whether the contrast-related metric value determined at block 856 indicates that the set of learn mode-refined light control parameters provide sufficiently optimal lighting. If so, then under this condition operation continues to the block 895, where the initial refined focus Z-height is used as the refined precise focus Z-height for the first focus region of interest (e.g., it is used as "the inspection value" Z-height for first focus region of interest, and/or to provide a "best focus" image for additional inspection operations). In other words, in a conditional run mode refinement implementation, if the set of refined light control parameters determined for the first focus region of interest during learn mode operations provide a sufficiently good value for a contrast-related metric under the conditions of block 856 during run mode, then those light control parameters are considered to be sufficiently optimum for use in precise autofocus operations for the corresponding first focus region of interest on a corresponding workpiece during run mode. In some embodiments, a limit for what constitutes a "sufficiently good value" at the decision block 858 may be determined based on experience and/or based on lighting sensitivity data acquired and analyzed during learn mode operations, for example as outlined previously with reference to FIG. 5. It will be appreciated that the conditional run mode lighting refinement implementation provides fast run mode execution based on the recalled learn mode-refined light control parameters when they are sufficient, but also initiates further run mode refinement of the light control parameters if they are not sufficiently optimal to insure the highest level of autofocus precision and repeatability. In particular, if it is determined at the decision block 858 whether the contrast-related metric value determined at block 856 indicates that the set of learn mode-refined light control parameters does not provide sufficiently optimal lighting, then under this condition operation continues to the block 860.

As shown in FIG. 8B, and described above, the operations of the blocks 860, 870, 880 and 890 may be used during an implementation including unconditional run mode refinement of the autofocus lighting parameters (e.g., by entry from point C, as outlined above), or an implementation including a conditional run mode refinement of the autofocus lighting parameters (e.g., by entry from the "no" condition of decision block 858, as outlined above). In either case, at the block 860 the machine vision inspection system is set at the quantitatively estimated initial refined focus Z-height determined at block 840, as a basis for providing further refined optimized lighting according to principles previously outlined with reference to FIGS. 3-5. Operation then continues at block 870.

At block 870, a set of refined light control parameters are automatically determined and/or learned based on at least one respective image of the first focus region of interest acquired using respective light control parameters at the initial refined focus Z-height set at block 860. Although a single image is sufficient for some situations as outlined previously, determining the set of refined light control parameters based on a plurality of images that use respective light control parameters may be more robust when a combination of lighting channels is used for illumination, or when workpiece characteristics not unpredictable, or when the highest possible accuracy is required, or the like. In any case, the set of refined light control parameters correspond to an image having a value for a contrast-related metric (e.g., a saturated pixel metric or a contrast metric) that is indicative that the set of refined light control parameters will provide a set of focus curve data that has a higher peak value than a peak value of the initial set of focus curve data. Various considerations related to contrast-related metrics and their use in determining a set of refined light control parameters have been outlined previously (e.g., particularly with reference to FIGS. 4 and 5) and the operations at block 870 may be configured accordingly.

Next, at the block 880, the precision machine vision inspection system is operated to provide a refined set of focus curve data for the first focus region of interest, based on the set of refined workpiece images acquired using the set of refined light control parameters determined at block 870. Then at block 890, the refined precise focus Z-height for the first focus region of interest is quantitatively estimated based on the refined set of focus curve data (e.g., according to previously outlined principles). In some embodiments, the refined precise focus Z-height is recorded as an inspection dimension. In other embodiments, the machine vision inspection system is positioned at the refined focus Z-height to obtain an image with the best possible focus in the first region of interest. It will be appreciated that execution of the operations of the blocks 860, 870, 880 and 890 during an implementation including unconditional or conditional run mode refinement of the autofocus lighting parameters always provides the best possible run mode autofocus precision and repeatability, according to previously outline principles.

One potential advantage of unconditional or conditional run mode refinement of the autofocus lighting parameters initially refined during learn mode is that various lighting configurations may be explored during learn mode, when throughput is not an issue and there is sufficient time to explore the effects of different lighting channels and/or their combinations (e.g., various ring light quadrants, co-axial light, stage light, various colors, etc.). Then during run mode, when throughput is more critical, the "refinement" may be constrained in certain implementations to simply altering the brightness of the previously "learned" or selected lighting channels, without altering which lighting channels are used. However, it will be appreciated that such an embodiment is exemplary only, and not limiting. In some embodiments, lighting channel selection may be altered during run mode, if desired.

In general, the refined lighting autofocus method of the present invention may be applied to a variety of applications. For example, in one application the method may be adapted when multiple regions of interest are present in a given field of view. In such instances, additional complexity may be involved, in that it may be desired to perform lighting optimization for each region of interest. In one embodiment, one set of optimum lighting parameters may be associated with a first region of interest within a field of view to be autofocused based on a first refined set of workpiece autofocus images, and then another set of optimum lighting parameters may be associated with another region of interest within the field of view to be autofocused based on another refined set of workpiece autofocus images. In one embodiment, one of more sets of optimum lighting parameters (e.g., the first set or another set of optimized lighting parameters) may be evaluated based on quantitatively well-focused images of a plurality of regions of interest in a field of view (e.g., based on evaluation of the value of a contrast-related metric in each respective region of interest) to determine if one set of optimized lighting parameters is sufficiently optimum for use in precise autofocusing for a plurality of regions of interest.

It will be appreciated that a precise refined lighting autofocus tool, mode or method according to this invention, may be applied to regions of interest with any arbitrary shape. It will also be appreciated that the application of these methods for measuring contrast in order to obtain desired lighting levels for specified operations (e.g., autofocus, edge detection, 3D reconstruction, etc.) may provide numerous advantages for operations related to surface autofocus, and/or edge autofocus, and/or to multiple "points from focus" 3D surface reconstruction in a region of interest, or the like. As previously outlined, such advantages include rapidly, automatically, and robustly providing the highest possible accuracy and repeatability for such autofocus related operations regardless of operator skill or judgment. Even when the associated increase in accuracy and repeatability is relatively small (e.g., at the sub-micron level for certain magnifications), it will be appreciated that even small improvements in the repeatability, accuracy and/or robustness of such autofocus operations are important in numerous applications, yet difficult to provide, particularly with regard to the measurement of certain difficult surfaces (e.g., highly variable textured surfaces), and in all cases greater accuracy is generally more desirable when performing precision measurement operations.

While the preferred embodiment of the invention has been illustrated and described, numerous variations in the illustrated and described arrangements of features and sequences of operations will be apparent to one skilled in the art based on this disclosure. Thus, it will be appreciated that various changes can be made therein without departing from the spirit and scope of the invention.

The embodiments of the invention in which an exclusive property or privilege is claimed are defined as follows:

1. A method for operating a precision machine vision inspection system to interdependently determine lighting parameters and a refined precise focus Z-height corresponding to a precise image focus for a first focus region of interest on a workpiece, the precision machine vision inspection system including an imaging portion, a controllable lighting portion, a focusing portion, and a control portion comprising an image processor, the method comprising:
  (a) illuminating the first focus region of interest on the workpiece with the controllable lighting portion controlled by an initial set of light control parameters;
  (b) operating the precision machine vision inspection system to provide an initial set of focus curve data for the first focus region of interest, based on an initial set of workpiece images acquired using the initial set of light control parameters at a plurality of Z-heights;
  (c) quantitatively estimating an initial focus Z-height based on the initial set of focus curve data for the first focus region of interest;
  (d) setting the precision machine vision inspection system at the initial focus Z-height for the first focus region of interest;
  (e) automatically determining a set of refined light control parameters based on at least one respective image of the first focus region of interest acquired using respective light control parameters at the initial focus Z-height, wherein the set of refined light control parameters are determined such that they correspond to an image having a value for at least one contrast-related metric that is indicative that the set of refined light control parameters will provide a set of focus curve data that has a higher peak value than a peak value of the initial set of focus curve data; and (f) performing at least one of the sets of operations (f1) and (f2), wherein (f1) comprises:
  (f1) storing the set of refined light control parameters in association with a part program for later use when inspecting a corresponding first focus region of interest on a corresponding workpiece,
and (f2) comprises:
  (f2) operating the precision machine vision inspection system to provide a refined set of focus curve data for the first focus region of interest, based on a set of refined workpiece images acquired using the set of refined light control parameters, and estimating the refined precise focus Z-height for the first focus region of interest, wherein the refined precise focus Z-height is quantitatively estimated based on the refined set of focus curve data.

2. The method of claim 1, wherein:
step (f) comprises performing the set of operations (f1); and
the method is performed during a learn mode of operation of the precision machine vision inspection system.

3. The method of claim 2, wherein precision machine vision inspection system comprises a graphical user interface and an autofocus video tool and at least the steps (b), (c), (d), and (e) are performed automatically by operations associated with the autofocus video tool.

4. The method of claim 3, further comprising user-selection and training of the autofocus video tool in a learn mode of operation of the precision machine vision inspection system in order to determine and store the set of refined light control parameters in correspondence to the first focus region of interest on the workpiece.

5. The method of claim 1, wherein:
step (f) comprises performing the set of operations (f2); and
the method is performed during a run mode of operation of the precision machine vision inspection system, wherein the precision machine vision inspection system is controlled by a part program.

6. The method of claim 1, wherein:
the method comprises performing the steps (a), (b), (c), (d), (e), and (f1) during a learn mode of operation of the precision machine vision inspection system, wherein during the learn mode of operation the first focus region of interest is a representative first focus region of interest on a representative workpiece; and
the operations of step (f2) are performed during a run mode of operation of the precision machine vision inspection system wherein, during the run mode of operation:
  the precision machine vision inspection system is controlled by the part program associated with operations of step (f1);
  the operations of step (f2) comprise recalling the stored set of refined light control parameters stored during the operations of step (f1) and using that set of refined light control parameters during the operations of step (f2); and
  the first focus region of interest on the workpiece is a current first focus region on a current workpiece which corresponds to the representative first focus region on the representative workpiece used during the learn mode of operation.

7. The method of claim 1, wherein:
the method comprises performing the steps (a), (b), (c), (d), (e), and (f1) during a learn mode of operation of the precision machine vision inspection system, wherein during the learn mode of operation the first focus region of interest is a representative first focus region of interest on a representative workpiece; and
the method comprises repeating the steps (a), (b), (c), (d), (e), and performing the operations of step (f2) during a run mode of operation of the precision machine vision inspection system, wherein, during the run mode operation:
  the precision machine vision inspection system is controlled by the part program associated with operations of step (f1);
  the operations of step (a) comprise recalling the stored set of refined light control parameters stored during the operations of step (f1) and using that set of refined light control parameters as the initial set of light control parameters during the run mode operations; and
  the first focus region of interest on the workpiece is a current first focus region on a current workpiece which corresponds to the representative first focus region on the representative workpiece used during the learn mode of operation.

8. The method of claim 1, wherein:
the method comprises performing the steps (a), (b), (c), (d), (e), and (f1) during a learn mode of operation of the precision machine vision inspection system, wherein during the learn mode of operation the first focus region of interest is a representative first focus region of interest on a representative workpiece; and
the method comprises repeating the steps (a), (b), (c), and performing conditional operations during a run mode of operation of the precision machine vision inspection system, wherein, during the run mode operation:
  the precision machine vision inspection system is controlled by the part program associated with operations of step (f1);
  the operations of step (a) comprise recalling the stored set of refined light control parameters stored during the operations of step (f1) and using that set of refined light control parameters as the initial set of light control parameters during the run mode operations; and
  the first focus region of interest on the workpiece is a current first focus region on a current workpiece which corresponds to the representative first focus region on the representative workpiece used during the learn mode of operation,
wherein the conditional operations comprise:
  after performing the operations of steps (a), (b), and (c) during the run mode of operations, determining the value of a contrast related metric for an image acquired using the set of light control parameters used during the run mode operations of steps (a) and (b) and at a Z-height proximate to the initial focus Z-height estimated in the run mode operations of step (c); and
  if the value of contrast related metric indicates that the set of light control parameters used during the run mode operations of steps (a) and (b) provide sufficiently optimal lighting, then using the initial focus Z-height estimated in the run mode operations of step (c) as the refined precise focus Z-height for the first focus region of interest.

9. The method of claim 8, wherein the conditional operations further comprise:
  if the value of contrast related metric indicates that the set of light control parameters used during the run mode operations of steps (a) and (b) do not provide sufficiently optimal lighting, then performing the operations of steps (d), (e), and step (f2) during the run mode of operation of the precision machine vision inspection system.

10. The method of claim 1, wherein in step (e) the at least one contrast-related metric comprises at least one of a pixel brightness metric, a saturated pixel metric, and a contrast metric.

11. The method of claim 1, wherein in step (e) the at least one respective image of the first focus region of interest comprises a plurality of respective images of the first focus region of interest acquired using respective light control parameters at the initial focus Z-height.

* * * * *